US012799225B2

(12) United States Patent
Alberti et al.

(10) Patent No.: US 12,799,225 B2
(45) Date of Patent: Nov. 17, 2026

(54) PLATFORM TO OBTAIN MONOCLONAL ANTIBODIES DIRECTED AGAINST PROCESSED TUMOR-SPECIFIC ANTIGENS

(71) Applicant: Mediterranea Theranostic srl, Lanciano (IT)

(72) Inventors: Saverio Alberti, Lanciano (IT); Marco Trerotola, Pescara (IT)

(73) Assignee: MEDITERRANEA THERANOSTIC S.R.L., Lanciano (IT)

( * ) Notice: Subject to any disclaimer, the term of this patent is extended or adjusted under 35 U.S.C. 154(b) by 658 days.

(21) Appl. No.: 18/259,000

(22) PCT Filed: Dec. 21, 2021

(86) PCT No.: PCT/EP2021/087122

§ 371 (c)(1),
(2) Date: Jun. 22, 2023

(87) PCT Pub. No.: WO2022/136452

PCT Pub. Date: Jun. 30, 2022

(65) Prior Publication Data

US 2024/0043557 A1 Feb. 8, 2024

(30) Foreign Application Priority Data

Dec. 22, 2020 (IT) ........................ 102020000031838

(51) Int. Cl.

| | |
|---|---|
| ***C07K 16/30*** | (2006.01) |
| ***A61K 39/395*** | (2006.01) |
| ***A61K 49/00*** | (2006.01) |
| ***A61P 35/00*** | (2006.01) |
| ***C12N 5/071*** | (2010.01) |
| ***G01N 33/575*** | (2026.01) |
| ***G01N 33/577*** | (2006.01) |

(52) U.S. Cl.

CPC ........ *C07K 16/30* (2013.01); *A61K 39/39558* (2013.01); *A61K 49/0004* (2013.01); *A61P 35/00* (2018.01); *C12N 5/0686* (2013.01); *G01N 33/5758* (2026.01); *G01N 33/577* (2013.01); *C07K 2317/34* (2013.01); *C07K 2317/92* (2013.01); *C12N 2502/30* (2013.01)

(58) Field of Classification Search

CPC ........................... C07K 16/30; C07K 2317/34; C07K 2317/92; A61K 39/39558; A61K 49/0004; A61P 35/00; A61P 35/04; C12N 5/0686; C12N 2502/30; G01N 33/5758; G01N 33/577; G01N 33/5759

See application file for complete search history.

(56) References Cited

U.S. PATENT DOCUMENTS

| | | | |
|---|---|---|---|
| 2011/0070156 | A1 | 3/2011 | Govindan et al. |
| 2012/0237518 | A1 | 9/2012 | Yamaguchi et al. |
| 2013/0122020 | A1 | 5/2013 | Liu et al. |
| 2017/0313781 | A1 | 11/2017 | Govindan et al. |

FOREIGN PATENT DOCUMENTS

| | | | |
|---|---|---|---|
| EP | 2393512 | A1 | 12/2011 |
| EP | 2573120 | A1 | 3/2013 |
| WO | 0105427 | A1 | 1/2001 |
| WO | 2007016590 | A2 | 2/2007 |
| WO | 2015047510 | A1 | 4/2015 |
| WO | 2016087651 | A1 | 6/2016 |
| WO | 2016172427 | A1 | 10/2016 |
| WO | 2017084763 | A1 | 5/2017 |

OTHER PUBLICATIONS

International Search Report for PCT/EP2021/087122 mailed Apr. 20, 2022, 8 pages.
Written Opinion of the ISA for PCT/EP2021/087122, mailed Apr. 20, 2022, 15 pages.
Federico Ambrogi et al."Trop-2 Is a Determinant of Breast Cancer Survival", Plos One, vol. 9, No. 5, Mar. 13, 2014, 11 pages.
Bignotti E et all "Trop-2 overexpression as an independent marker for poor overall survival in ovarian carcinoma patients", European Journal of Cancer, Elsevier, Amsterdam NL, vol. 46, No. 5, Mar. 1, 2010, pp. 944-953.

*Primary Examiner* — Robert S Cabral
(74) *Attorney, Agent, or Firm* — Silvia Salvadori, P.C.; Silvia Salvadori

(57) ABSTRACT

It forms an object of the present invention a method to obtain monoclonal antibodies, or fragments or conjugates thereof, which bind with high affinity to a target protein which is a protein specifically expressed in local and metastatic tumors, preferably said target protein being Trop-2, wherein said method comprises: —making available an immunogenic material, wherein the immunogenic material is selected in the group comprising the target protein, fragments and conjugates thereof produced in different organisms, including tumor cells that naturally express the processed target protein and mammalian transformed and tumor cells, insect cells, yeast cells, bacterial cells that have been transfected with vectors that express the target protein and fragments thereof, also as fusion proteins with other sequences; —administering to a non-human animal one of said immunogenic material.

8 Claims, 26 Drawing Sheets

Specification includes a Sequence Listing.

MARGPGLAPPPLRLPLLLLVLAAVTGHTAAQDNCTCPT
NKMTVCSPDGPGGRCQCRALGSGMAVDCSTLTSKCLLL
KARMSAPKNARTLVRPSEHALVDNDGLYDPDCDPEGRF
KARQCNQTSVCWCVNSVGVRRTDKGDLSLRCDELVRTH
HILIDLRHRPTAGAFNHSDLDAELRRLFRERYRLHPKF
VAAVHYEQPTIQIELRQNTSQKAAGEVDIGDAAYYFER
DIKGESLFQGRGGLDLRVRGEPLQVERTLIYYLDEIPP
KFSMKRLT*AGLIAVIVVVVALVAGMAVLVI*TNRRKSG
KYKKVEIKELGELRKEPSL

Leader: aa 1-30

Globular domain: aa 31-145

Stem: aa 146-274

*Transmembrane: aa 275-297*

Cytoplasmic tail: aa 298-323

Fig. 1

Figure 2:
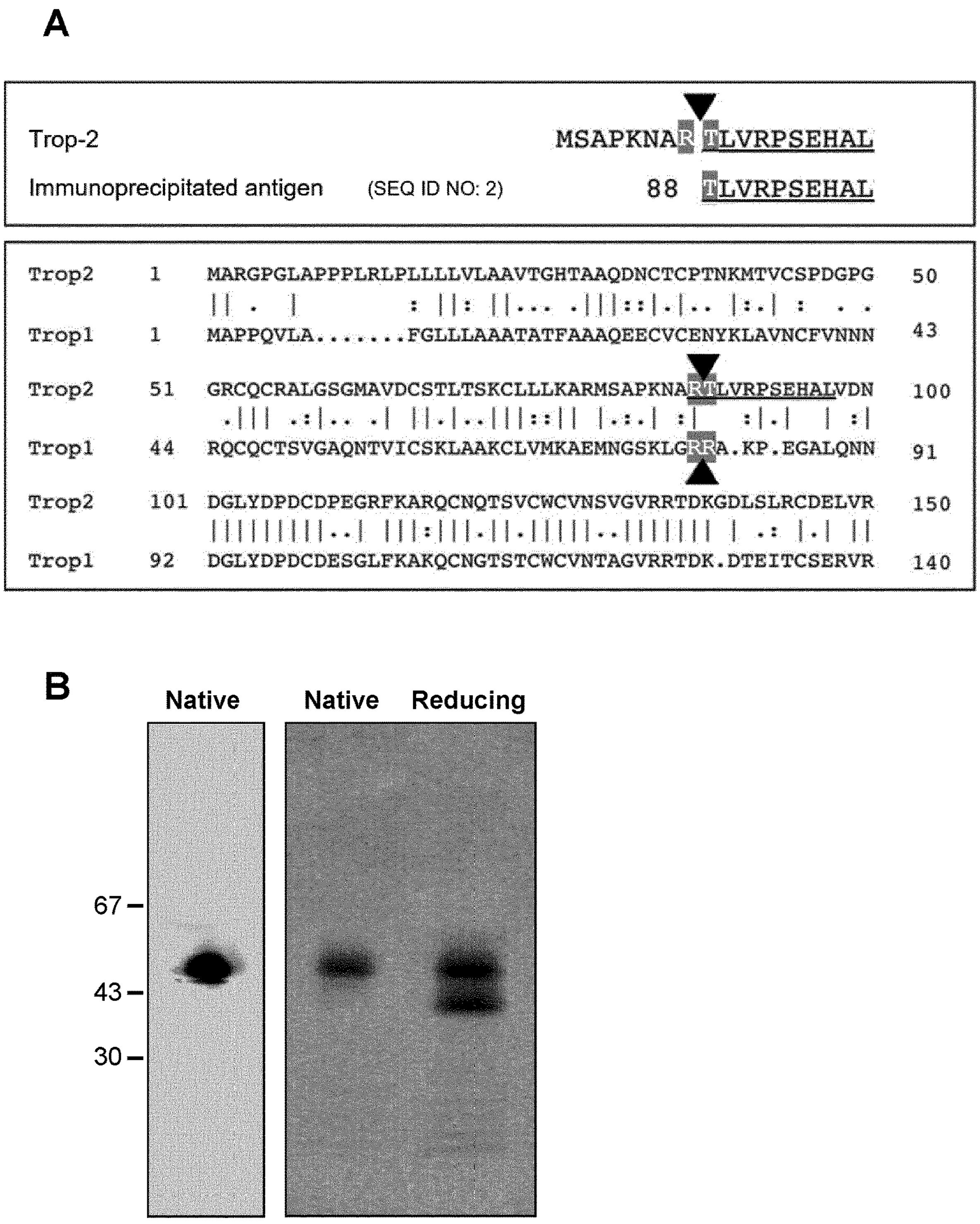

C
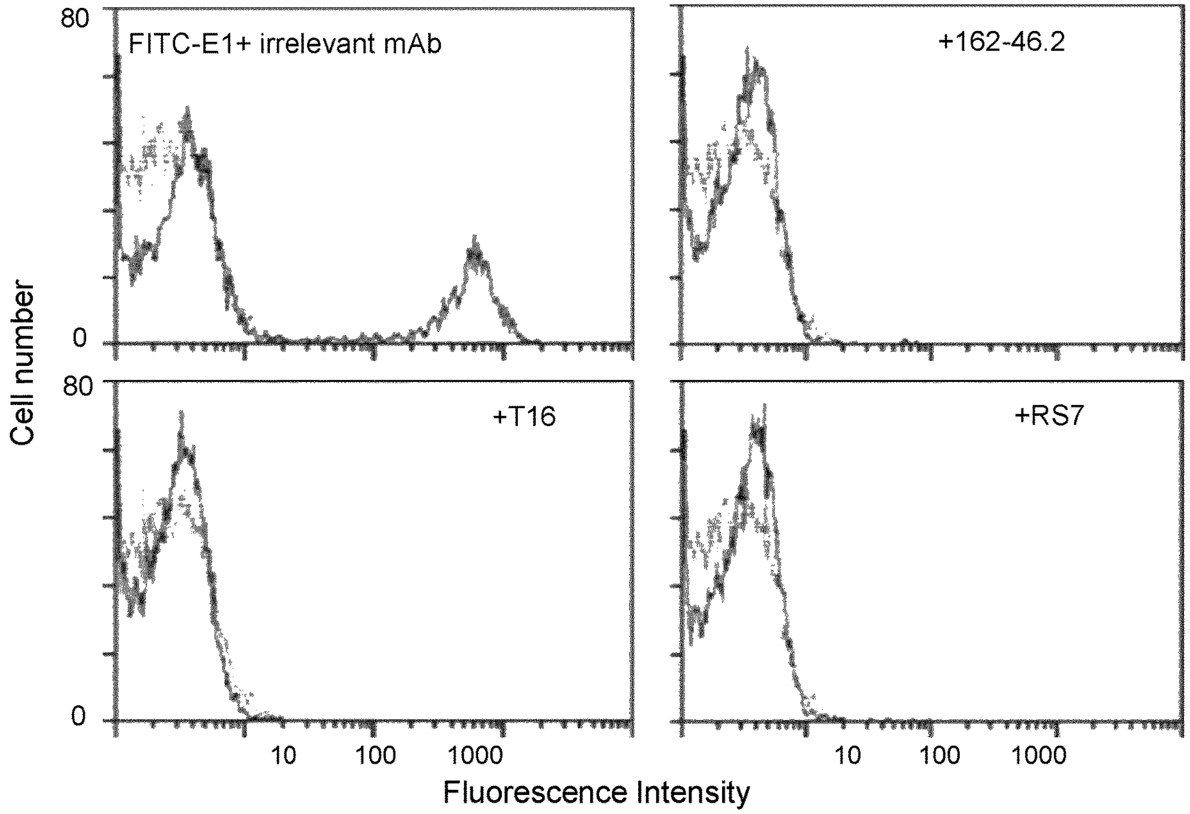
D
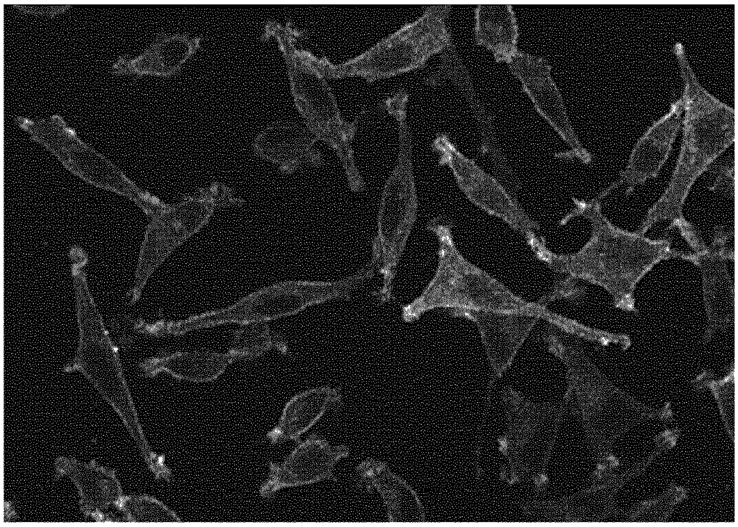
Fig. 2

```
        lhhhhhhh-----------------------------llllllllllllllleeelllleeeeeeeellllleeeeeelllleeellllllllllll
```

```
        lhhhhhhh-----------------------------lllllllllllleeellleeeeeeeelllleeeeeeellleeelllllllllll

p41     TKCQEEVS-----------------------------HIPAVHPGSFRPKCDENGNYLPLQCYGSIGYCWCVFPNGTEVPNTRSRGHHNC
Trop-2  SKCLLLKARMSAPKNARTLVRPSEHALVDNDGLYDPD-------------CDPEGRFKARQCNQT-SVCWCVNSVGVRRTD-KGDLSLRC

        lhhhhhhhlllllllllllllllllllllllllllle-------------eellleeeeeeeell-leeeeelllllllll-llllllll
```

Fig. 3A

E

| Processing sites of ADAM10 substrates | | | | | | | | | | | |
|---|---|---|---|---|---|---|---|---|---|---|---|
| Substrate | Uniprot code | P5 | P4 | P3 | P2 | P1 | P1' | P2' | P3' | P4' | SEQ ID NO |
| Amyloid-beta precursor protein | P05067 | Glu | Val | His | His | Gln | Lys | Leu | Val | Phe | SEQ ID NO: 3 |
| Amyloid-beta precursor protein | P05067 | Gly | Val | Val | Ile | Ala | Thr | Val | Ile | Val | SEQ ID NO: 4 |
| Amyloid-beta precursor protein | P05067 | Val | Gly | Gly | Val | Val | Ile | Ala | Thr | Val | SEQ ID NO: 5 |
| Amyloid-beta precursor protein | P05067 | Val | His | His | Gln | Lys | Leu | Val | Phe | Phe | SEQ ID NO: 6 |
| Calsyntenin-1 | O94985-2 | Ala | Asn | His | Met | Ala | Ala | Gln | Pro | Gln | SEQ ID NO: 7 |
| Calsyntenin-1 | O94985-2 | Glu | His | Ala | Asn | His | Met | Ala | Ala | Gln | SEQ ID NO: 8 |
| Calsyntenin-1 | O94985-2 | Ala | Thr | Val | Val | Ile | Val | Val | Cys | Val | SEQ ID NO: 9 |
| Calsyntenin-1 | O94985-2 | Pro | Ser | Thr | Ala | Thr | Val | Val | Ile | Val | SEQ ID NO: 10 |
| Calsyntenin-2 | Q9H4D0 | Glu | His | Val | Asn | His | Leu | Ile | Val | Gln | SEQ ID NO: 11 |
| Calsyntenin-2 | Q9H4D0 | Ala | Thr | Val | Val | Ile | Ile | Ile | Ser | Val | SEQ ID NO: 12 |
| Calsyntenin-2 | Q9H4D0 | Pro | Ser | Ile | Ala | Thr | Val | Val | Ile | Ile | SEQ ID NO: 13 |
| Calsyntenin-3 | Q9BQT9 | Ala | His | Pro | Ser | His | Val | Leu | Ser | Ser | SEQ ID NO: 14 |
| Calsyntenin-3 | Q9BQT9 | Ala | Thr | Leu | Ile | Ile | Val | Val | Cys | Val | SEQ ID NO: 15 |
| Calsyntenin-3 | Q9BQT9 | Pro | Ser | Ala | Ala | Thr | Leu | Ile | Ile | Val | SEQ ID NO: 16 |
| CD40 ligand | P29965 | Asn | Ser | Phe | Glu | Met | Gln | Lys | Gly | Asp | SEQ ID NO: 17 |
| Delta-like 1 | Q61483 | Leu | Ser | Glu | Arg | His | Met | Glu | Ser | Gln | SEQ ID NO: 18 |
| Ephrin type-B receptor 2 | P54763 | Ala | Glu | Tyr | Gln | Thr | Ser | Ile | Lys | Glu | SEQ ID NO: 19 |
| Heparin-binding EGF-like growth factor | Q06186 | Thr | Pro | Ser | Lys | Glu | Arg | Asn | Gly | Lys | SEQ ID NO: 20 |
| Heparin-binding EGF-like growth factor | Q06186 | Lys | Lys | Lys | Gly | Lys | Gly | Leu | Gly | Lys | SEQ ID NO: 21 |
| Heparin-binding EGF-like growth factor | Q06186 | Glu | Asn | Pro | Leu | Tyr | Thr | Tyr | Asp | His | SEQ ID NO: 22 |
| Major prion protein | P04156 | Thr | Asn | Met | Lys | His | Met | Ala | Gly | Ala | SEQ ID NO: 23 |
| Major prion protein | P04925 | Ala | Tyr | Tyr | Asp | Gly | Arg | Arg | Ser | - | SEQ ID NO: 24 |
| Myelin basic protein | P02687 | Tyr | Leu | Ala | Ser | Ala | Ser | Thr | Met | Asp | SEQ ID NO: 25 |
| Myelin basic protein | P02687 | Gly | His | His | Ala | Ala | Arg | Thr | Thr | His | SEQ ID NO: 26 |
| Myelin basic protein | P02687 | Tyr | Gly | Ser | Leu | Pro | Gln | Lys | Ala | Gln | SEQ ID NO: 27 |
| Myelin basic protein | P04370 | Tyr | Gly | Ser | Leu | Pro | Gln | Lys | Ser | Gln | SEQ ID NO: 28 |
| Neurogenic locus notch homolog protein 1 | Q01705-1 | Tyr | Lys | Ile | Glu | Ala | Val | Lys | Ser | Glu | SEQ ID NO: 29 |
| Low affinity neurotrophin receptor p75NTR | P07174 | Gly | Ser | Ser | Gln | Pro | Val | Val | Thr | Arg | SEQ ID NO: 30 |
| Low affinity neurotrophin receptor p75NTR | P07174 | Gln | Pro | Val | Val | Thr | Arg | Gly | Thr | Thr | SEQ ID NO: 31 |

Fig. 4

E con.

| Processing sites of ADAM10 substrates | | | | | | | | | | | |
|---|---|---|---|---|---|---|---|---|---|---|---|
| Substrate | Uniprot code | P5 | P4 | P3 | P2 | P1 | P1' | P2' | P3' | P4' | SEQ ID NO |
| Protrasforming growth factor alpha | P01135 | Pro | Val | Ala | Ala | Ala | Val | Val | Ser | His | SEQ ID NO: 32 |
| Tumor necrosis factor | P01375 | Pro | Leu | Ala | Gln | Ala | Val | Arg | Ser | Ser | SEQ ID NO: 33 |
| Probetacellulin | P35070 | Ser | Pro | Glu | Thr | Asn | Leu | Leu | Cys | Gly | SEQ ID NO: 34 |
| Probetacellulin | P35070 | Val | Asp | Leu | Phe | Tyr | Leu | Arg | Gly | Asp | SEQ ID NO: 35 |
| EGF | P01133 | His | Tyr | Ser | Val | Arg | Asn | Ser | Asp | Ser | SEQ ID NO: 36 |
| EGF | P01133 | Trp | Trp | Glu | Leu | Arg | His | Ala | Gly | His | SEQ ID NO: 37 |
| E-cadherin | P12830 | Arg | Lys | Ala | Gln | Pro | Val | Glu | Ala | Gly | SEQ ID NO: 38 |
| N-cadherin | P19022 | Thr | Asp | Val | Asp | Arg | Ile | Val | Gly | Ala | SEQ ID NO: 39 |
| CD23 | P06734 | Ala | Glu | Gln | Gln | Arg | Leu | Lys | Ser | Gln | SEQ ID NO: 40 |
| CD23 | P06734 | Gly | Asp | Gln | Met | Ala | Gln | Lys | Ser | Gln | SEQ ID NO: 41 |
| CD23 | P06734 | Leu | Arg | Ala | Glu | Gln | Gln | Arg | Leu | Lys | SEQ ID NO: 42 |
| Fas ligand | P48023 | His | Thr | Ala | Ser | Ser | Leu | Glu | Lys | Gln | SEQ ID NO: 43 |
| Eukaryotic translation initiation factor 1 | P48024 | Ser | Ser | Leu | Glu | Lys | Gln | Ile | Gly | His | SEQ ID NO: 44 |

Fig. 4

| m/z | MH+matched | Intensity | Delta ppm | Start | End | Missed cleavages | Sequence | SEQ ID NO |
|---|---|---|---|---|---|---|---|---|
| 5.5 | 12817161 | 1058.2 | -65.4 | 241 | 252 | 0 | (R)HYEGLSYNVDSLHQKHQR(A) | SEQ ID NO: 46 |
| 16,998,917 | 16,998,874 | 3303.1 | 2.5 | 196 | 211 | 1 | (R)QRPRESYQMGHMR(R) | SEQ ID NO: 47 |
| 17,078,259 | 17,077,802 | 3697.3 | 26.7 | 736 | 748 | 1 | (R)AHPEKHAASSGPELLR(K) | SEQ ID NO: 48 |
| 22,111,842 | 2,211,069 | 27627.0 | 52.4 | 31 | 48 | 1 | (R)EAVIAQISSHVK(A) | SEQ ID NO: 49 |
| 12,816,323 | 12,817,161 | 1058.2 | -65.4 | 241 | 252 | 0 | (R)HYEGLSYNVDSLHQKHQR(A) | SEQ ID NO: 46 |
| 16,998,917 | 16,998,874 | 3303.1 | 2.5 | 196 | 211 | 1 | (R)QRPRESYQMGHMR(R) | SEQ ID NO: 47 |
| 17,078,259 | 17,077,802 | 3697.3 | 26.7 | 736 | 748 | 1 | (R)AHPEKHAASSGPELLR(K) | SEQ ID NO: 48 |

Fig. 6A

B

ADAM 10 SEQ ID NO:50

```
  1 MVLLRVLILL LSWAAGLGGQ YGNPLNKYIR HYEGLSYNVD SLHQKHQRAK RAVSHEDQFL
 61 LLDFHAHGRQ FNLRMKRDTS LFSDEFKVET SNKVLDYDTS HIYTGHIYGE EGSFSHGSVI
121 DGRFEGFIKT RGGTFYIEPA ERYIKDRILP FHSVIYHEDD INYPHKYGPQ GGCADHSVFE
181 RMRKYQMTGV EEGARAHPEK HAASSGPELL RKKRTTLAER NTCQLYIQTD HLFFKYYGTR
241 EAVIAQISSH VKAIDTIYQT TDFSGIRNIS FMVKRIRINT TSDEKDPTNP FRFPNIGVEK
301 FLELNSEQNH DDYCLAYVFT DRDFDDGVLG LAWVGAPSGS SGGICEKSKL YSDGKKKSLN
361 TGIITVQNYG SHVPPKVSHI TFAHEVGHNF GSPHDSGTEC TPGESKNLGQ KENGNYIMYA
421 RATSGDKLNN NKFSLCSIRN ISQVLEKKRN NCFVESGQPI CGNGMVEQGE ECDCGYSDQC
481 KDDCCFDANQ PEGKKCKLKP GKQCSPSQGP CCTAQCAFKS KSEKCRDDSD CAKEGICNGF
541 TALCPASDPK PNFTDCNRHT QVCINGQCAG SICEKYDLEE CTCASSDGKD NKELCHVCCM
601 KKMAPSTCAS TGSLQWSKQF SGRTITLQPG SPCNDFRGYC DVFMRCRLVD ADGPLARLKK
661 AIFSPQLYEN IAEWIVAHWW AVLLMGIALI MLMAGFIKIC SVHTPSSNPK LPPPKPLPGT
721 LKRRRPPQPI QQPPRQRPRE SYQMGHMRR
```

Fig. 6

Figure 7:
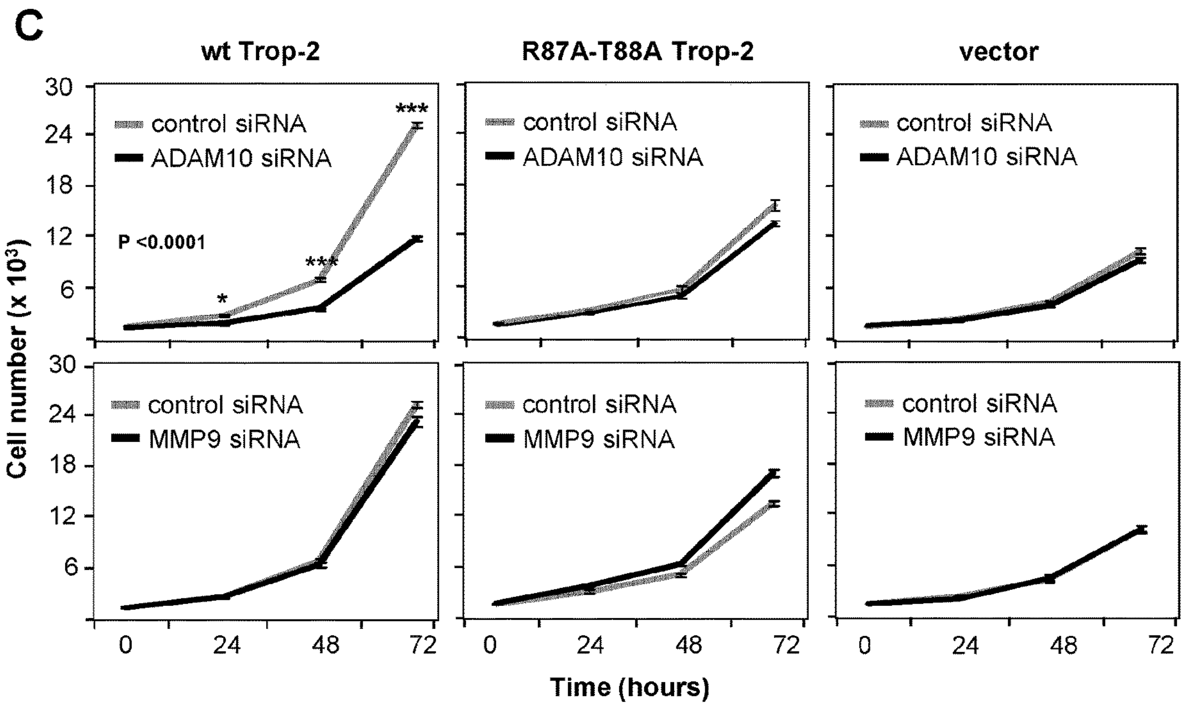

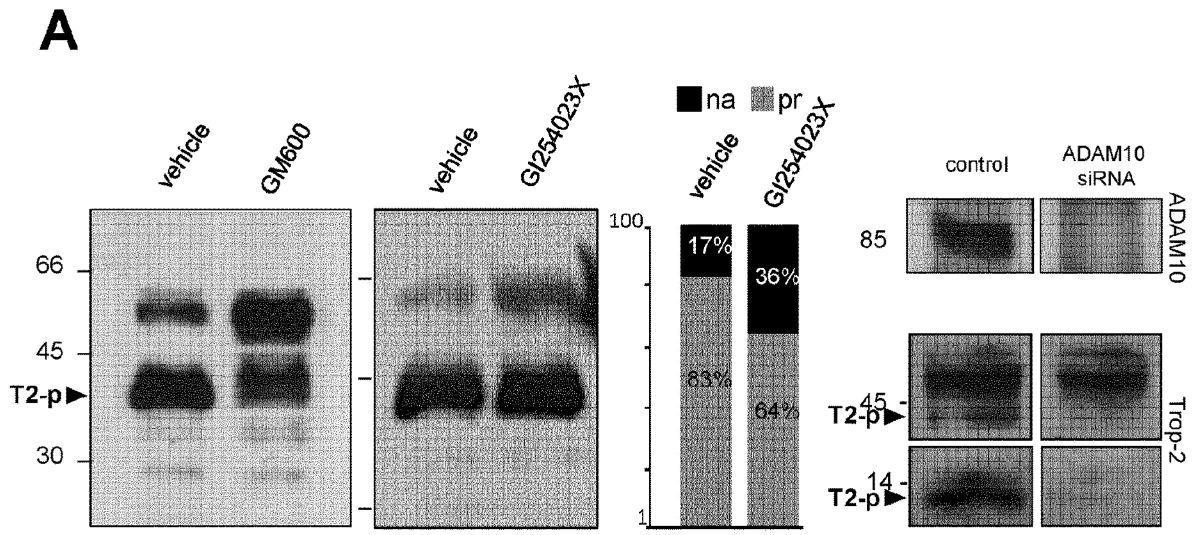
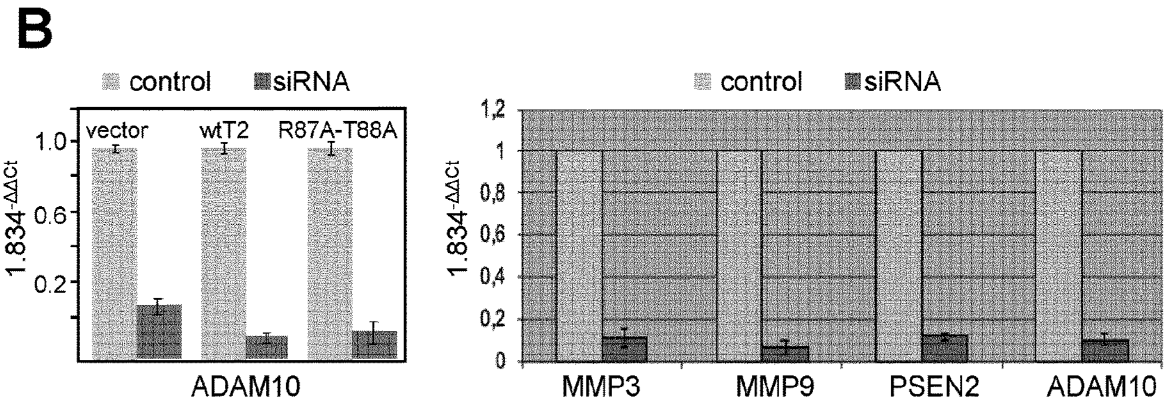
Fig. 7

Figure 9:
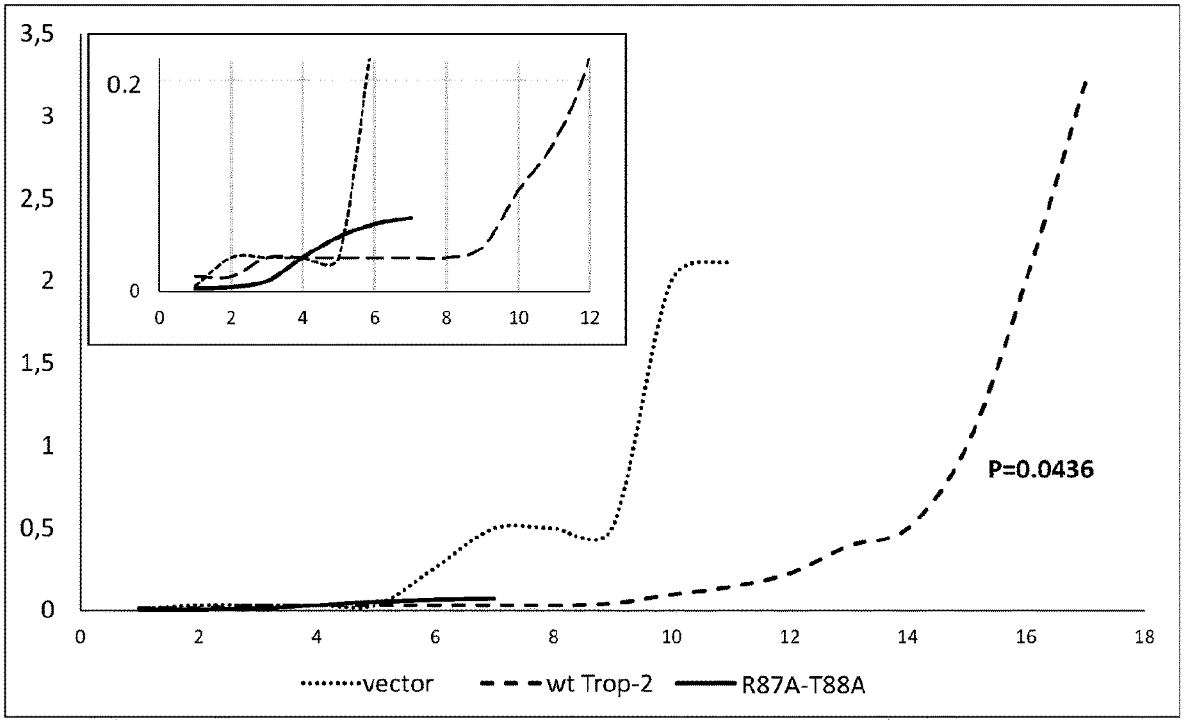

A
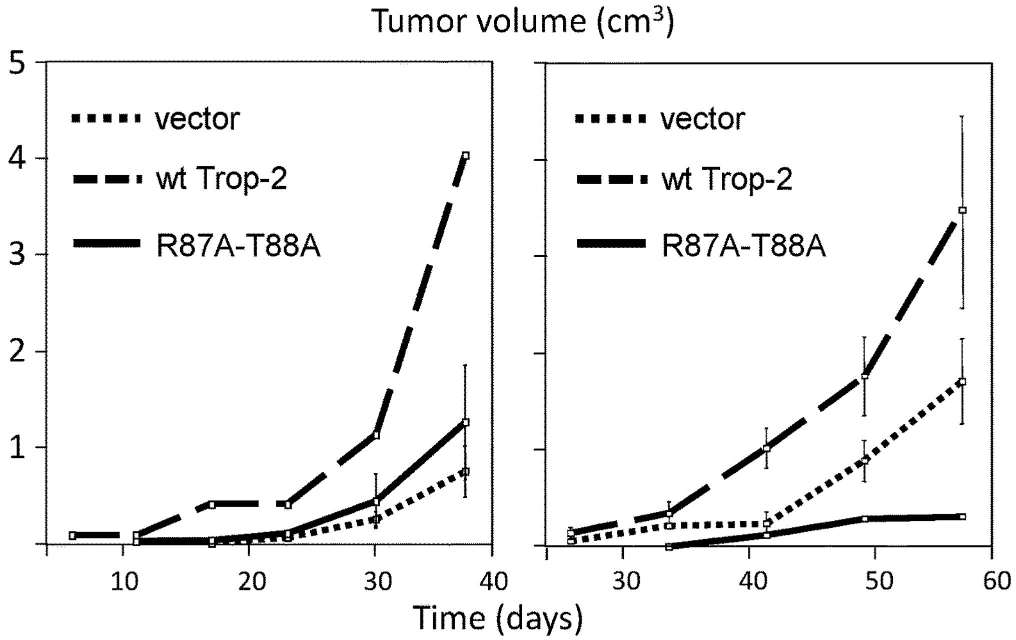
B
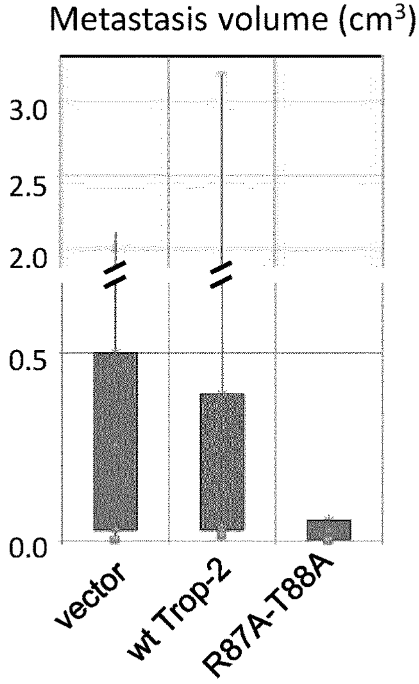
Fig. 9

C

Figure 10A:
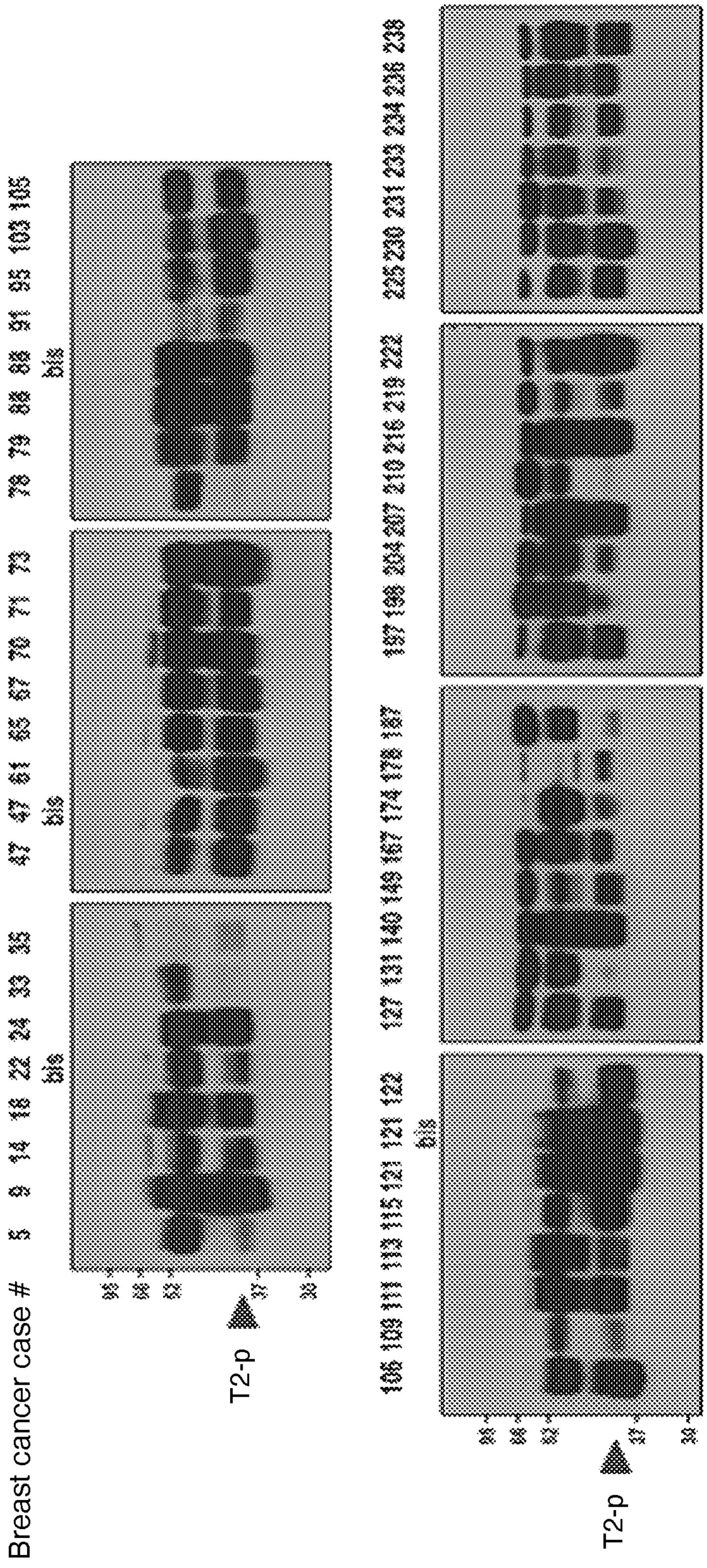

B
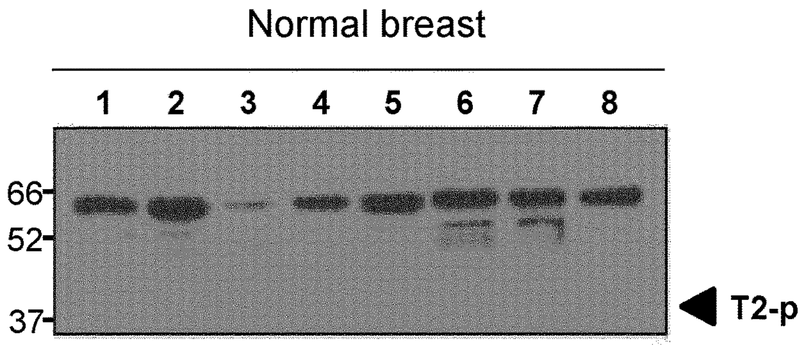
C
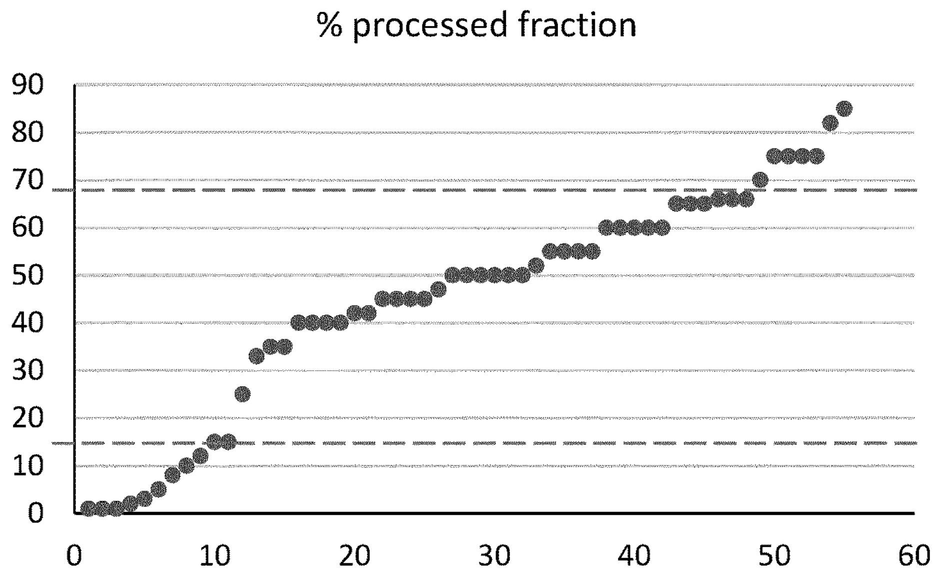
Fig. 10

Figure 11:
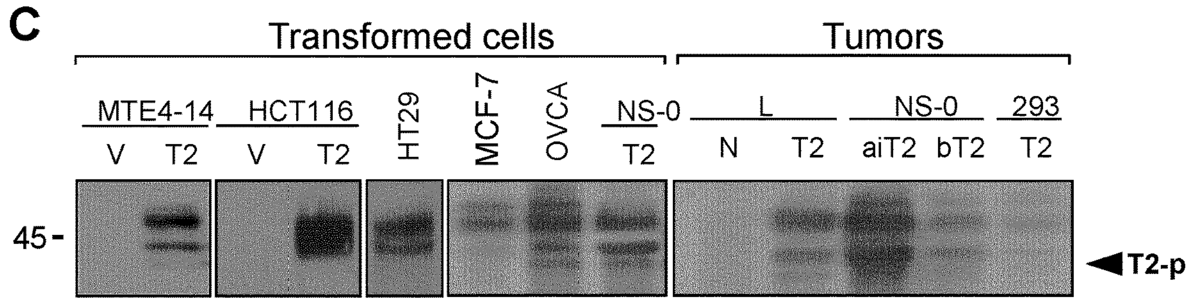

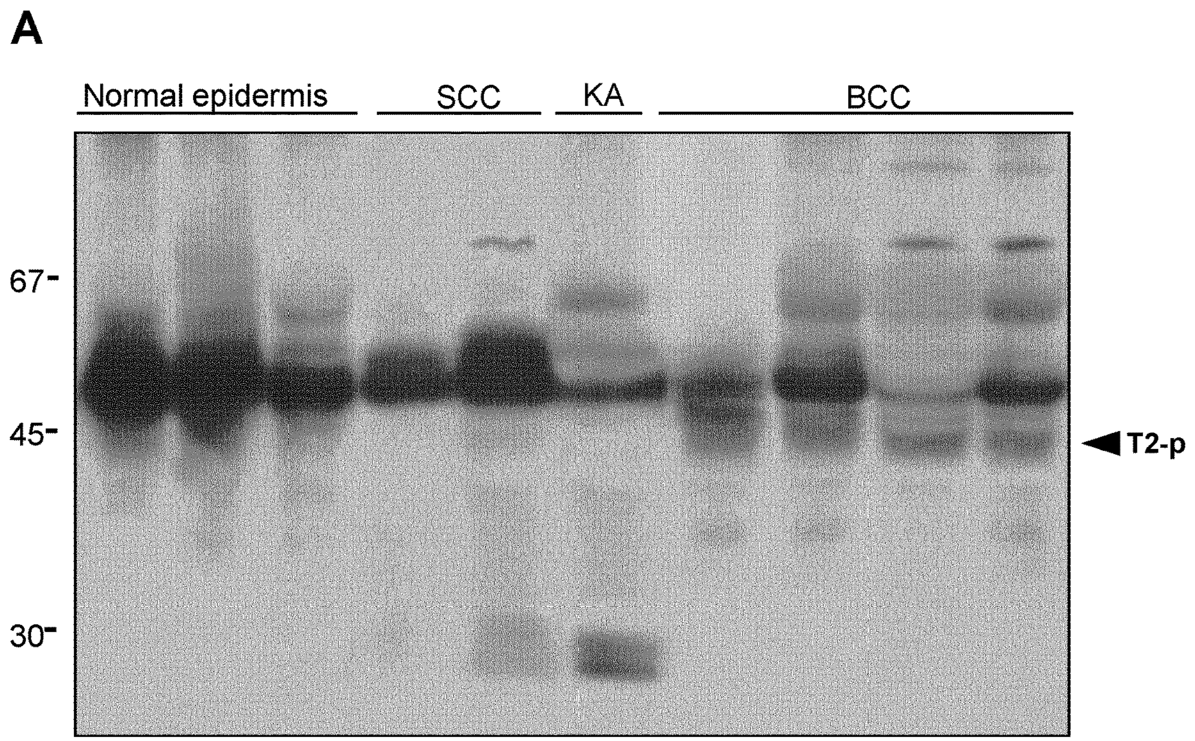
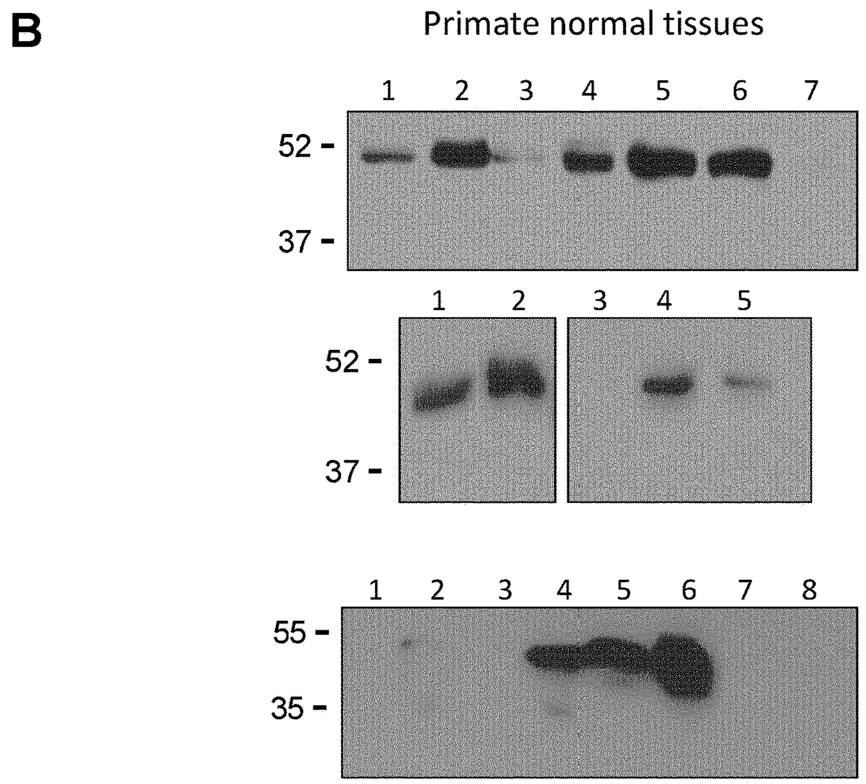
Fig. 11

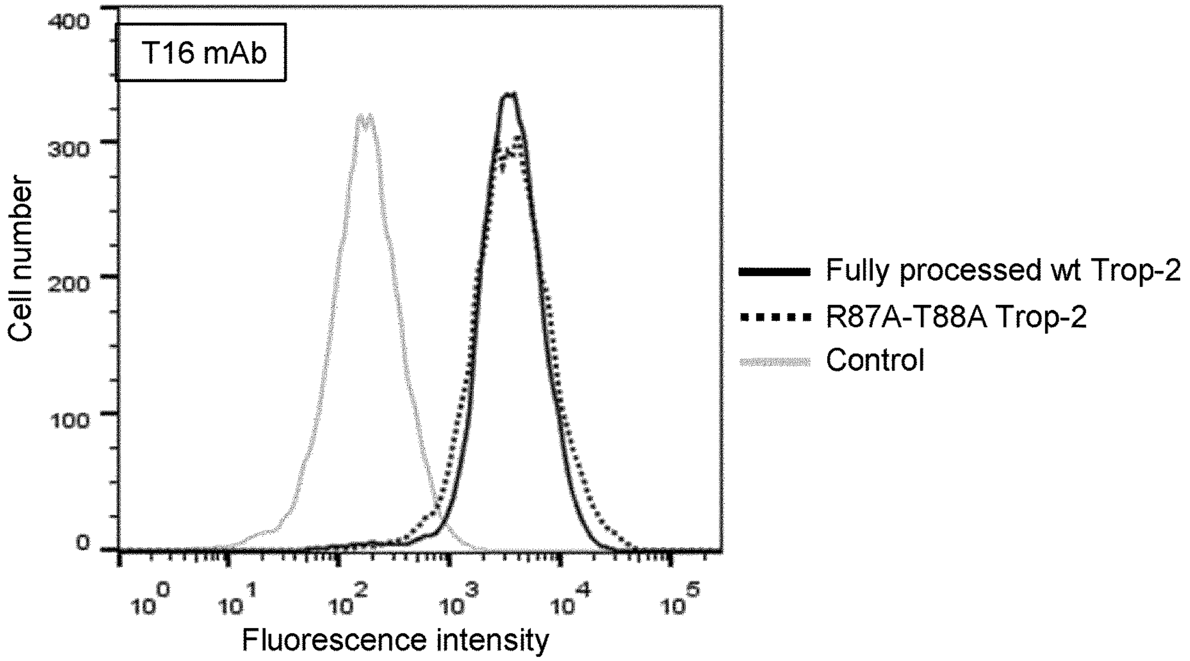
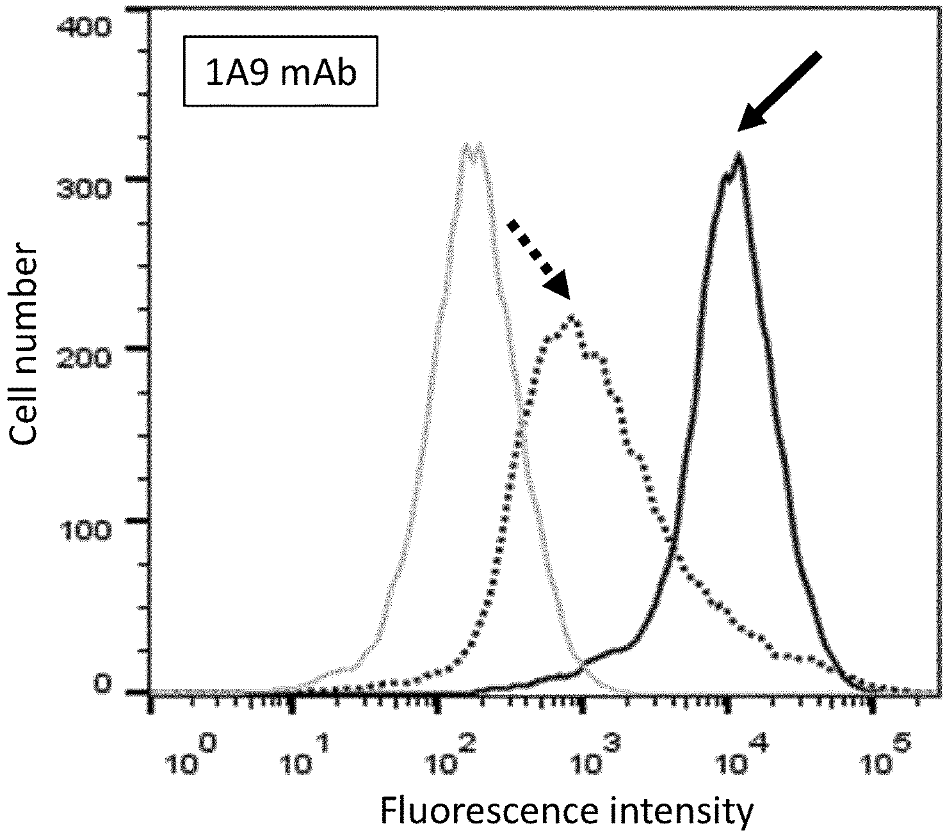
Fig. 13

PLATFORM TO OBTAIN MONOCLONAL ANTIBODIES DIRECTED AGAINST PROCESSED TUMOR-SPECIFIC ANTIGENS

CROSS-REFERENCE TO RELATED APPLICATIONS

This application is the U.S. national phase of International Application No. PCT/EP2021/087122 filed Dec. 21, 2021 which designated the U.S. and claims priority to IT 102020000031838 filed Dec. 22, 2020, the entire contents of each of which are hereby incorporated by reference.

TECHNICAL FIELD

The present invention concerns a platform to obtain monoclonal antibodies, fragments, and conjugates thereof that bind with high affinity processed, tumor-specific forms of proteins, for medical and industrial uses. More specifically, the invention concerns a method to obtain monoclonal antibodies, fragments, and conjugates thereof that are able to bind with high affinity the Trop-2 protein in the processed form that is specific for tumors. The use of such method includes the diagnostic, prognostic, and therapeutic fields of Trop-2-expressing malignancies. The related tumors include, but are not limited to, cancers of the breast, head and neck, skin, colon-rectum, stomach, lung, ovary, thyroid, prostate, pancreas, endometrium, cervix, gallbladder, bile ducts, kidney, urinary bladder and choriocarcinomas.

STATE OF THE ART

Trop-2 (NCBI accession number: NP_002344.2; SEQ ID NO: 1) is also known as tumor-associated calcium signal transducer 2 (TACSTD-2), GA733-1, EGP, MR23, MR54, RS-7 and T16. Trop-2 localizes along the cell membrane in epithelia and functions as a signal transducer that induces an intracellular calcium signal after cross-linking with antibodies and activates a growth-signaling network that converges on AKT (Guerra, Trerotola et al. 2016).

The extracellular domain of the Trop molecules (Trop-2 and the Trop-1/EpCAM paralog, with NCBI accession number NP_002345.2) contains a GA-733 (EGF-like) domain and a thyroglobulin repeat, that host 12 conserved cysteine residues. This cysteine-rich region folds as a globular domain (amino acids 31-145 of SEQ ID NO: 1) and is followed by a region devoid of cysteines (amino acids 146-274 of SEQ ID NO: 1), that acts as a connecting “stem” to the transmembrane domain (FIG. 1). Trop-2 molecules engage in homophylic interactions between adjacent cells and establish multimeric complexes with tight-junction proteins. Both EGF-like and thyroglobulin domains are involved in homophylic intra- and inter-membrane interactions in the case of the Trop-1/Ep-CAM molecule (Zanna, Trerotola et al. 2007).

Trop-2 is overexpressed by most cancer cells in man (Trerotola, Cantanelli et al. 2013). Overexpression was found in breast cancer cells, in bladder cancer, ovarian serous papillary carcinomas, and in numerous other tumors, e.g., non-small cell lung cancer, choriocarcinomas, colo-rectal, prostate, and endometrial cancers. Transformation of keratinocytes with SV40 induced a 3- to 4-fold higher expression of Trop-2 compared to their normal counterparts (Schon and Orfanos 1995), consistent with a direct role in tumor progression. The authors of the present invention have shown that Trop-2 drives cancer development and progression through interaction and regulation of expression of several proteins involved in cell-cell and cell/matrix adhesion in epithelial tissues. Upregulation of TROP2 was shown to be both necessary and sufficient to stimulate tumor growth, and Trop-2 was found to induce growth in direct proportion to its expression levels. Further, expression of Trop-2 has been associated with poor prognosis of pancreatic, gastric, lung, oral, ovarian, and colo-rectal cancers. More specifically, membrane overexpression of Trop-2 was associated with unfavorable prognosis of breast cancer (Ambrogi, Fornili et al. 2014). The authors of the present invention have also shown that Trop-2 can be revealed in intracellular compartments, in a heterogeneous manner across different tumor cases (Trerotola, Cantanelli et al. 2013) and that high intracellular Trop-2 expression levels are associated with improved outcome in breast cancer (Ambrogi, Fornili et al. 2014), thus indicating the usefulness of measuring Trop-2 sub-cellular localization for prognostic procedures.

Metastatic disease is the dominant cause of death in cancer patients, and is the greatest hurdle for cancer cure, as metastatic cancer is largely resistant to therapy. The identification of proteins/genes linked to the metastatic phenotype is useful, as these markers can contribute to the identification of the aggressive cases at an early stage and provide new targets for novel therapies. This research was conducted by the authors of the present invention, who looked for genes that were concordantly dysregulated across independent cancer metastasis models. Following this approach, the authors of the present invention showed that TROP2 was the only gene consistently upregulated in metastatic cancers across different experimental settings, tumor types, and animal species. A large-scale analysis of Trop-2 expression in human primary cancers and their corresponding metastases revealed Trop-2 overexpression in the metastases from colon, stomach, breast, and ovary tumors. Trop-2 overexpression was then shown to drive metastasis and to affect the outcome of colon, stomach, breast, pancreas, lung, and ovary cancers. This showed that Trop-2 is an inducer of tumor progression and metastatic diffusion (Guerra, Trerotola et al. 2008, Trerotola, Rathore et al. 2010, Stoyanova, Goldstein et al. 2012, Trerotola, Cantanelli et al. 2013).

The high expression levels of Trop-2 in many human tumors and in their metastases have made this molecule an attractive target for “adoptive” immunotherapy, i.e., based on the administration of experimentally produced antibodies.

WO2010089782 and WO2016087651 describe anti-Trop-2 monoclonal antibodies able to recognize and bind different regions of the Trop-2 molecule with high efficiency for diagnostic and therapeutic uses in cancer.

Sacituzumab govitecan-hziy, a humanized anti-Trop-2 monoclonal antibody conjugated to the SN-38 topoisomerase I inhibitor, was shown to be effective in patients with metastatic triple-negative breast cancer (TNBC) (Bardia, Mayer et al. 2019) and was granted accelerated FDA approval as Trodelvy, for use in the clinics (www.fda.gov/drugs/drug-approvals-and-databases/drug-tral-snapshot-trodelvy). This indicated that Trop-2-targeted monoclonal antibodies can be useful to generate drugs to treat cancer, including advanced cases that have progressed to metastasis.

Technical Problem

Trop-2 expression is not exclusively limited to tumors. Trop-2 is also expressed in normal human tissues, at high levels in skin, oesophagus, tonsils, cornea, at lower levels in lung, exocrine pancreas, prostate, salivary glands, urothelium, bile ducts, breast, kidney, and sometimes in the stomach and in the endometrium. Unlike Trop-1, which is expressed by proliferating epithelial cells, Trop-2 is expressed predominantly by epithelial cells at advanced stages of differentiation. In the epidermis the expression of Trop-2 is detected in the keratinocytes of the suprabasal layer and increases towards the surface of the skin, with the highest expression levels in the stratum corneum.

Antigen expression in normal tissues poses serious problems of on-target toxicity that strongly limit the use of high-potency targeted therapeutics. A phase-1 dose-escalation study of bivatuzumab mertansine, which targets the tumor-associated v6-containing CD44 variant, also expressed in skin keratinocytes and other epithelia, showed serious skin toxicity and one fatal event due to the development of massive epidermal necrolysis after the second infusion at the highest dose (Tijink, Buter et al. 2006). BAY794620, an ADC targeting the CA9 antigen, also expressed within the gut, showed fatal gastrointestinal toxicity in two patients (Clinical Study Report No.: PH-37705/12671. Bayer Healthcare, 2014). Specifically, for Trop-targeted anti-cancer therapy, adverse effects were observed in patients that involved organs that normally express the molecule. The high-affinity humanized anti-Trop-1 monoclonal antibody ING-1 caused cases of acute pancreatitis in patients (de Bono, Tolcher et al. 2004). Moreover in a recent phase 1, dose-escalation study in patients with advanced or metastatic solid tumors the anti-Trop-2/Aur0101 antibody-drug conjugate PF-06664178 showed excess toxicity that manifested with neutropenia, skin rash and mucosal inflammation (King, Eaton et al. 2018). In both these cases clinical development was terminated.

Obtaining tumor-specific monoclonal antibodies would allow the design of novel targeted drugs that combine high antitumor potency and low on-target toxicity for a highly improved therapeutic index. Classical oncogenes/tumor suppressors acquire transforming capabilities following mutations in coding or regulatory sequences. Recurrent, high-frequency oncogenic mutations that alter the amino acid sequence may offer potential for tumor-specific targeting. However, this is not the case for Trop-2: while germline mutations of the TROP2 gene have been described and cause the inherited corneal amyloidosis known as Gelatinuos Drop-Like Dystrophy (GDLD) (Tsujikawa, Kurahashi et al. 1999), Trop-2 is substantially wild-type in tumors (Trerotola, Cantanelli et al. 2013).

Solutions to the Technical Problem

To improve the effectiveness of targeted anticancer therapy with monoclonal antibodies, while at the same time preventing toxicity, it is important that such monoclonal antibodies recognize specific epitopes of the target molecule that are exposed in tumor cells. This makes also possible to bind higher numbers of tumor cells, when the epitopes of the individual antibodies are selectively expressed at different developmental stages of the tumor, while sparing normal cells.

The authors of the present invention have discovered here that Trop-2 post-translational processing by ADAM10 is a feature of malignancies. 3D modeling of Trop-2 structure predicts that such processing causes a spatial rearrangement of the extracellular portion of the molecule and the consequent exposure of domains that would be normally inaccessible. These domains provide novel tumor-specific targets. Therefore, it is object of the present invention a platform that uses immunization methods to obtain monoclonal antibodies, fragments, and conjugates thereof with maximal epitope heterogeneity, and screening methods of such antibodies, fragments, and conjugates thereof for differential recognition of the antigen in tumors versus normal tissues. This platform can be applied to proteins that undergo tumor-specific processing, to obtain monoclonal antibodies, fragments, and conjugates thereof that specifically bind to cancer tissues, thus providing means to reduce the toxicity of targeted therapies and to improve anticancer therapies.

DESCRIPTION OF THE INVENTION

Post-translational processing is a key activator step of several tumor growth inducers and adhesion molecules. The present invention refers to a platform to obtain monoclonal antibodies, fragments, and conjugates thereof, that are specific for such processed forms It is therefore an object of the present invention a method to obtain monoclonal antibodies, or fragments or conjugates thereof, which recognise and bind with high affinity processed proteins that are specifically expressed in local and metastatic tumors, said method characterized by immunization and screening procedures according to the present invention.

Protein lysates from tumor cells are typically used as immunogenic material in procedures aimed to obtain monoclonal antibodies targeting tumor antigens. However, this may result in establishing one main (immunodominant) epitope that will correspondingly skew antibody generation and produce one single antibody species even from independent immunization procedures. This was shown by the Authors of the present invention who found that the anti-Trop-2 162-46.2 obtained through immunization with the human choriocarcinoma BeWo cell line (Lipinski, Parks et al. 1981), T16, obtained through immunization with bladder cancer cells (Fradet, Cordon-Cardo et al. 1986), and RS7-3G11 monoclonal antibody obtained through immunization with tissue from lung squamous carcinoma (U.S. Pat. No. 7,238,785B2) all recognize the same epitope, which is also expressed in normal tissues (Fradet, Cordon-Cardo et al. 1986). Hence an object of the present invention are immunization procedures aimed to increase the probability to obtain monoclonal antibodies able to recognize diverse epitopes, wherein the immunogenic material consists of the target protein or fragments or conjugates thereof produced in different organisms, including tumor cells that naturally express the processed target protein and mammalian transformed and tumor cells, insect cells, yeast cells, that have been transfected with vectors that express the full-length target protein or fragments or conjugates thereof. Different domains of the target protein can be expressed as fusion proteins with tags that improve immunogenicity of small, non-immunogenic peptides, triggering the production of a wider variety of antibodies. These tags can also provide useful element for the visualization and purification of the corresponding fusion proteins.

Another object of the present invention consists of screening procedures especially designed to select monoclonal antibodies able to access and bind the target protein in its tumor-specific processed form. Therefore a specific object of the present invention is a method that comprises the steps of: a) contacting the target protein in its tumor-specific processed form with each one of the monoclonal antibodies or fragments or conjugates thereof under screening; b) measuring the binding between the target protein in its tumor-specific processed form and each one of the monoclonal antibodies or fragments or conjugates thereof under screening; c) contacting the target protein in its normal-tissue unprocessed form with each one of the monoclonal antibodies or fragments or conjugates thereof under screening; d) measuring the binding between the target protein in its normal-tissue unprocessed form and each one of the monoclonal antibodies or fragments or conjugates thereof under screening; e) contacting a negative control, comprising or consisting of protein or proteins different from the target protein and/or cells that do not express the target protein; f) measuring the binding between the negative control and the monoclonal antibody or fragments or conjugates thereof; g) selecting the monoclonal antibodies or fragments or conjugates thereof that show absence of binding to the negative control and binding to the target protein in its tumor-specific processed form that is at least 10 times higher than the binding to the target protein in its normal-tissue unprocessed form. These different steps can be performed sequentially or in parallel. This binding between antigen and antibody, fragments and conjugates thereof can be measured by flow cytometry and/or ELISA assay and/or cell-based ELISA assay and/or microscopy and/or bio-layer interferometry and/or isothermal titration calorimetry and/or microscale thermophoresis and/or surface plasmon resonance.

The target protein in its processed form can be expressed by tumors that express it endogenously or can be expressed by tumor cells that have been transfected with suitable vectors. The target protein in its unprocessed form can be expressed by normal tissues that express it endogenously or can be expressed by normal cells that have been transfected with suitable vectors. The negative control can be a protein or proteins different from the target protein, or cells that do not express the target protein, or cells that do not express the target protein and have been transfected with the empty vector. Expressing and non-expressing cells can be identified by means of target-specific antibodies that are already known in the art. The negative control can comprise or consist of negative cells that have been transfected with the empty vector. Using transfectants with expression vectors for the target protein and with the empty vector as negative control offers a stringent comparison as the target protein is the only variable between the two systems. The target protein can be in its wild-type form or can be engineered at the processing sites, to make them either constitutively fully activated or inactivated/processing-resistant.

In a preferred object of the present invention the processing of the target protein is post-translational and comprises at least one of the modifications selected from the group consisting of: peptide bond cleavage, amino acid modifications, including deamidation, addition of chemical groups, including phosphorylation, acetylation, hydroxylation, methylation, addition of complex organic molecules, including lipidation, AMPylation, ubiquitination, SUMOylation. More preferably the processing consists of the cleavage of at least one peptide bond of the target protein.

In a preferred embodiment, said target protein is Trop-2 and said immunogenic material is selected in the group comprising: a peptide consisting of the extra-cellular portion of Trop-2, AA 31-274 of SEQ ID NO: 1, a peptide consisting of the globular domain of Trop-2, AA 31-145 of SEQ ID NO: 1, a peptide consisting of the “stem” domain of Trop-2, AA 146-274 of SEQ ID NO: 1.

In an embodiment, said peptides are produced in native form in one of the following: transformed human kidney epithelial 293, breast adenocarcinoma MCF-7, murine cells of fibrosarcoma L and NS-0 myeloma, Sf9 moth cells, yeast cells, or, in non-native form, in *Escherichia Coli* cells.

In a preferred object of the present invention the tumors where specific processing occurs include cancers of the breast, head and neck, skin, colon-rectum, stomach, lung, ovary, thyroid, prostate, pancreas, endometrium, cervix, gallbladder, bile ducts, kidney, urinary bladder, choriocarcinomas, and their metastases.

An object of the present invention is a platform to obtain monoclonal antibodies or fragments, or conjugates thereof directed against processed tumor-specific antigens for use as a medicament, preferably for use in the prevention and/or treatment of tumors and metastases, more preferably of the tumors and metastases that express Trop-2, even more preferably in combination with at least one therapeutic agent or treatment. In an object of the present invention, the therapeutic agents are cytotoxic substances, including radioactive isotopes, chemotherapeutic agents, and toxins of bacterial, fungal, plant or animal origin, and their fragments. A chemotherapeutic agent is a chemical compound useful in the treatment of cancer, including doxorubicin, 5-fluorouracil, cytosine-arabinoside (“Ara-C”), cyclophosphamide, thiotepa, busulfan, taxol, methotrexate, cisplatin, melphalan and other nitrogen mustards, vinblastine, bleomycin, etoposide, ifosfamide, mitomycin C, mitoxantrone, vincristine, vinorelbine, carboplatin, teniposide, aminopterin, dactinomycin, esperamycins. The therapeutic agent can be an intercellular mediator, for example a cytokine, including non-exclusively lymphokines, monokines, hormones, growth factors, interferon, interleukins, coming from natural sources or from recombinant cell cultures, as well as biologically active equivalents of native cytokines. Therapeutic treatments can be surgical removal of the tumor and related metastases, and/or radiotherapy.

Another object of the present invention is a platform to obtain monoclonal antibodies or fragments or conjugates thereof directed against processed tumor-specific antigens for use in the diagnosis and/or prognosis of tumors or metastases, in assessing the risk of developing a tumor or metastases, in monitoring the progression of a tumor or metastases, in monitoring the efficacy of an antitumor or antimetastasis therapeutic treatment, in the screening of antitumor or antimetastasis therapeutic treatments.

It forms a further object of the present invention an antibody specific for Trop-2 protein expressed in local or metastatic tumor, wherein said antibody binds to a non-linear epitope on Trop-2 comprise between glycosylated residues N120 and N208, wherein said epitope is on Trop-2 protein cleaved between R87 and T88, wherein the residue numbering is according to SEQ ID NO. 1.

Said non-linear epitope has been surprisingly identified on 3D Trop-2 structure, PDB ID: 7PEE.

In an embodiment, said non-linear is selected in the group comprising: a peptide consisting of the extra-cellular portion of Trop-2, AA 31-274 of SEQ ID NO: 1, a peptide consisting of the globular domain of Trop-2, AA 31-145 of SEQ ID NO: 1, a peptide consisting of the “stem” domain of Trop-2, AA 146-274 of SEQ ID NO: 1.

In an embodiment, said peptides are produced in native form in one of the following: transformed human kidney epithelial 293, breast adenocarcinoma MCF-7, murine cells of fibrosarcoma L and NS-0 myeloma, Sf9 moth cells, yeast cells or, in non-native form, in *Escherichia Coli* cells.

In an embodiment, said antibody is 1B4, secreted by the hybridoma deposited with the International Depositary Authority (IDA): Interlab Cell Line Collection, IRCCS Ospedale Policlinico San Martino, Genova, Italy, and assigned accession number PD21005.

In an embodiment, said antibody is 1A9, secreted by the hybridoma deposited with the International Depositary Authority (IDA): Interlab Cell Line Collection, IRCCS Ospedale Policlinico San Martino, Genova, Italy, and assigned accession number PD21006.

It forms a further object of the present invention a pharmaceutical composition comprising at least one, preferably one antibody according to the present invention.

In a further embodiment, it forms an object of the present invention said pharmaceutical composition for use in a method for treating a human subject for a cancer.

INDUSTRIAL APPLICABILITY

The present invention finds application in the field of monoclonal antibody generation for clinical use, where it teaches new immunization procedures and screening methods to obtain specificity towards processed tumor-specific forms of target proteins. Hybridomas that produce monoclonal antibodies can be obtained through techniques known in the art, by fusion of immunoglobulin-producing cells isolated from immunized animals, for example from the spleen of Balb-C mice, with cells from immortalized cell lines, for example murine myeloma lines. Immunization can take place through injections of immunogenic material in compositions and according to methods and schedules of administration known in the art. In one embodiment of the present invention the immunogenic material contains the target protein that has been produced by various organisms, such as human tumor cells that naturally express the target protein and transformed or tumor mammalian cells, insect cells, yeast cells that have been transfected with vectors that express the whole target protein, its fragments and/or conjugates. Cancer cells include, but are not limited to, cells from cancers of the breast, head and neck, skin, colorectal, stomach, lung, ovary, thyroid, prostate, pancreas, endometrium, cervix, gallbladder, bile ducts, kidney, urinary bladder, and cells from choriocarcinomas. Transformed cells include, but are not limited to, 293 human embryonic kidney cells that have been transformed with adenoviral DNA.

A nucleic acid molecule that codes for the target protein or mutated forms or fragments or conjugates thereof according to the present invention can be generated according to technologies known in the art, for example PCR amplification of template molecules or gene synthesis. A fragment of the target protein can be, in the case of membrane proteins, the extracellular portion. A fragment of the target protein can also be a particular structural and/or functional domain, that is identified based on sequence homology, structure predictions, structure determinations or functional studies known in the art. The target protein can be conjugated by means of recombinant DNA technologies known in the art to fluorescent molecules, enzymes, or specific sequences (tags) to obtain fusion proteins for detection, purification, and to increase immunogenicity. Specific sequences can also be added to the N-terminus to guide secretion (leader sequences). Conjugation can also per performed with the inclusion of linker sequences that are positioned upstream of the tag and can be cut in vitro by enzymes known in the art to obtain the native target protein. Examples of tags to facilitate purification include the 6-histidine tail, glutathione S-transferase, maltose-binding protein, chitin-binding protein, FLAG sequence, myc-tag, hemagglutinin. Tags to increase immunogenicity are known in the art and include immunoglobulin domains and short peptide chains formed by 2 glycine residues followed by 5 isoleucine or 5 proline or 5 arginine residues.

The nucleic acid molecule can be cloned into an expression vector by means of recombinant DNA technologies known in the art. Plasmid and viral expression vectors are known that are suitable for various eukaryotic organisms, such as mammals, insects, yeasts, and prokaryotes, such as bacteria. The vector for the expression of the target protein or mutated forms, fragments, or conjugates thereof can be inserted into the host cells through chemical transfection or by electroporation. Transfection methods are known in the art and transfection kits and electroporation equipment are available on the market. Viral expression vectors can be transfected into competent host cells together with vectors coding for viral structural proteins, to obtain viruses that can infect the host cells that will be used for the production of the recombinant protein. For example, viruses can be baculoviruses, lentiviruses, retroviruses, adenoviruses, adeno-associated viruses.

The cells that express the target protein, fragments or conjugates thereof can be grown in culture media and conditions known in the art. In one embodiment, the immunogen can contain the target protein that has been purified from cell lysates and/or from culture media in which its soluble forms are secreted. In another embodiment, the immunogen can derive from unfractionated cell lysates and/or culture media as above. The target protein, fragments or conjugates thereof can be purified by experts in the art using procedures known in the art, for example affinity chromatography or molecular exclusion chromatography. A fragment of the target protein can be, in the case of membrane proteins, the extracellular portion, which can thus be secreted into the culture medium.

The monoclonal antibody screening method according to the present invention measures and compares the binding of the antibody to the tumor-specific processed target protein, fragments, or conjugates thereof with the binding to the unprocessed target protein, fragments or conjugates thereof expressed by untransformed normal cells, and with the negative control as defined above. Methods for measuring antibody-antigen binding are known in the art. In one embodiment, the method is flow cytometry, in which the amount of antibody, fragments or conjugates thereof is measured that bind to each cell expressing the antigen, preferably a membrane antigen and preferably expressed by living cells, for example live tumor cell lines and cells isolated from primary tumors and metastases, or transfected cells. The expression of the target protein in its processed and unprocessed forms is detected by antibodies known in the art that are not tumor specific. The processing is performed on the wild-type target protein by the specific molecular machinery of the tumor cell. Flow cytometry measurement is performed by measuring the fluorescence that is associated with the antibody, directly if the antibody is conjugated to a fluorescence molecule, or indirectly if the antibody is bound by a secondary antibody that is conjugated to a fluorescent molecule. Fluorescent molecules with specific emission and excitation spectra and corresponding flow cytometers are known in the art.

In one embodiment of the present invention antibody-antigen binding is measured by cell-based ELISA assays or by optical or fluorescence microscopy, using antibodies or secondary antibodies that are labelled by enzymatic or fluorescent tags. In another aspect of the present invention antibody-antigen binding is measured by classical ELISA assays on target proteins, fragments, or conjugates thereof that have been purified from endogenously expressing or transfected tumor cells and from cells isolated from normal tissues. In another aspect of the present invention antibody-antigen binding is measured by bio-layer interferometry, isothermal titration calorimetry, microscale thermophoresis, surface plasmon resonance.

The present invention will be now described by way of illustration and example, according, but not limited, to, some of its preferred embodiments, with reference to the figures of the enclosed drawings.

FIG. 1. Trop-2 sequence.

Amino acid sequence of Trop-2 (SEQ ID NO: 1). The different regions of the molecule are indicated; aa: amino acids.

FIG. 2. Purification, sequencing, and analysis of Trop-2 immunoprecipitated from tumor cells.

A. (top) Alignment between the amino acid sequence obtained by Edman degradation of the E1 immunoprecipitate (underlined; SEQ ID NO: 2) and the canonical Trop-2 sequence (aa 88-97 of SEQ ID NO: 1); (bottom) alignment between the proteolytic sites of Trop-2 and Trop-1 (Schön, Schön et al. 1993). Arrowhead: cleavage site.

B. (left) Western blotting (WB) of purified Trop-2, run in SDS-PAGE gradient gel under native (non-reducing) conditions; (right) Coomassie blue staining of purified Trop-2 run under native or reducing conditions, as indicated.

C. Competition studies between the E1 antibody and anti-Trop-2 monoclonal antibodies (mAbs) known in the art were performed by staining reconstituted mixtures of 70% parental L cells and 30% L/TROP2 transfectants with the FITC-E1 mAb after preincubation with 100× excess of each of the indicate mAbs. Competition between antibodies, which depends on recognition of a shared epitope, was revealed by the disappearance of the peak of FITC-E1 stained cells. Irrelevant mAb: mAb that does not recognize Trop-2. Black line: FITC-E1 stained sample; gray line: unstained sample:

D. Immunofluorescence confocal microscopy image of L/TROP2 transfectants stained with the FITC-E1 mAb.

Figure 3:
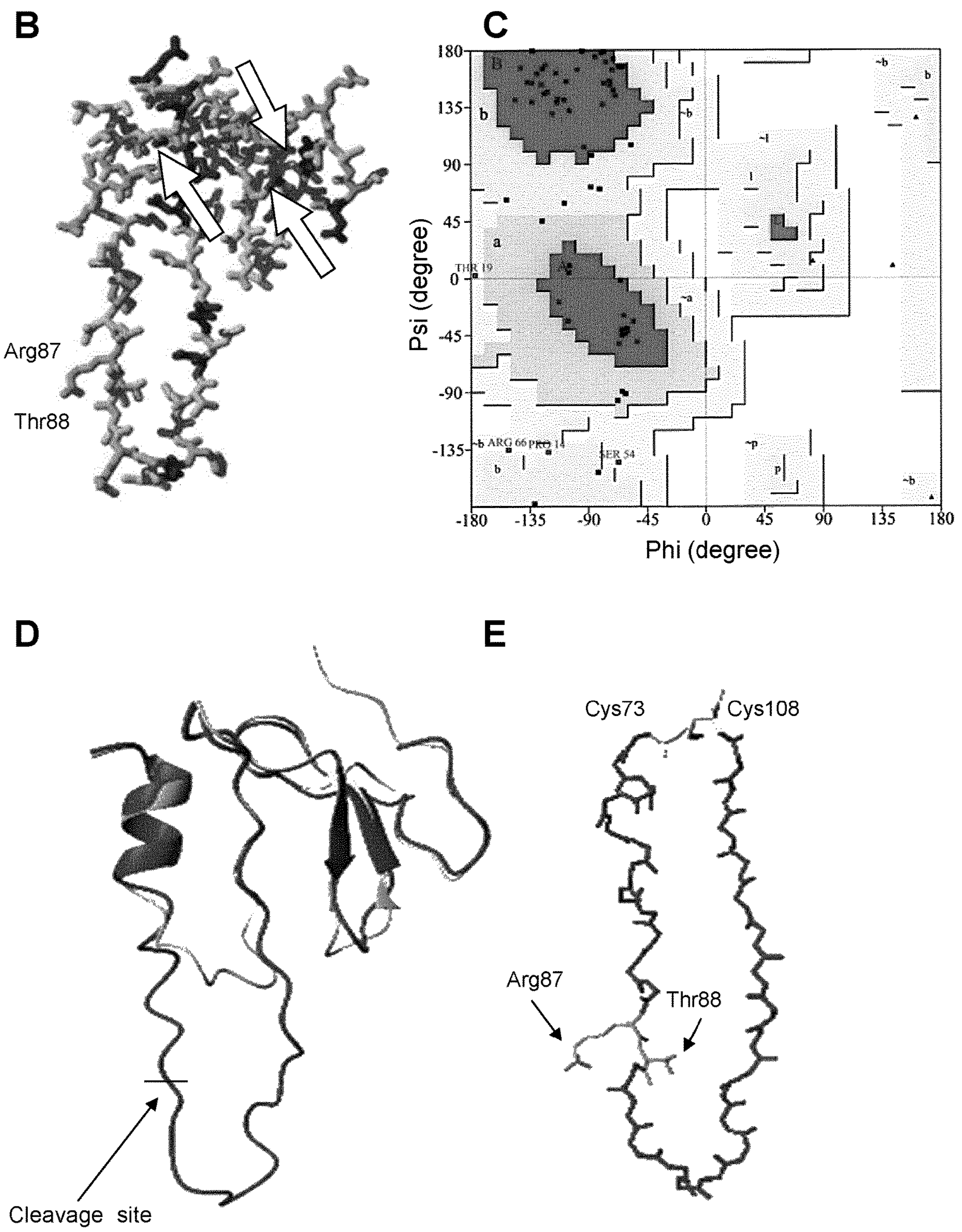

FIG. 3. Structure of the Trop-2 thyroglobulin domain.

Generation of the 3D model of the thyroglobulin domain of Trop-2 (aa 71-145 of SEQ ID NO: 1), using homology modeling approaches and the p41 structure as template (aa 211-271 of the sequence with NCBI accession number: NP_001020330.1).

A. Alignment between the amino acid sequence of the protein under study (Trop-2) and that of the template protein (p41), to generate an input file for structure homology-modelling.

B. RODS-Raster3D stick representation of the 3D structure of Trop-2 thyroglobulin domain. Amino acid residues of different classes are indicated in different shades of gray. The three white arrows indicate the disulfide bridges. The Arg87 and Thr88 amino acids are indicated that flank the processing site.

C. Ramachandran plot of the Trop-2 thyroglobulin domain; the conformations that do not have any steric hindrance (core regions) are shown in dark gray.

D. 3D MOLMOL ribbon diagram of superimposed Trop-2 thyroglobulin domain (dark gray) and corresponding p41 domain (light gray). The cleavage site is indicated by the arrow.

E. 3D backbone of the first loop of the Trop-2 thyroglobulin domain. The two cysteines that are engaged in a disulfide bridge and the two amino acid residues flanking the cleavage site are indicated, with their side chains.

Figure 4:
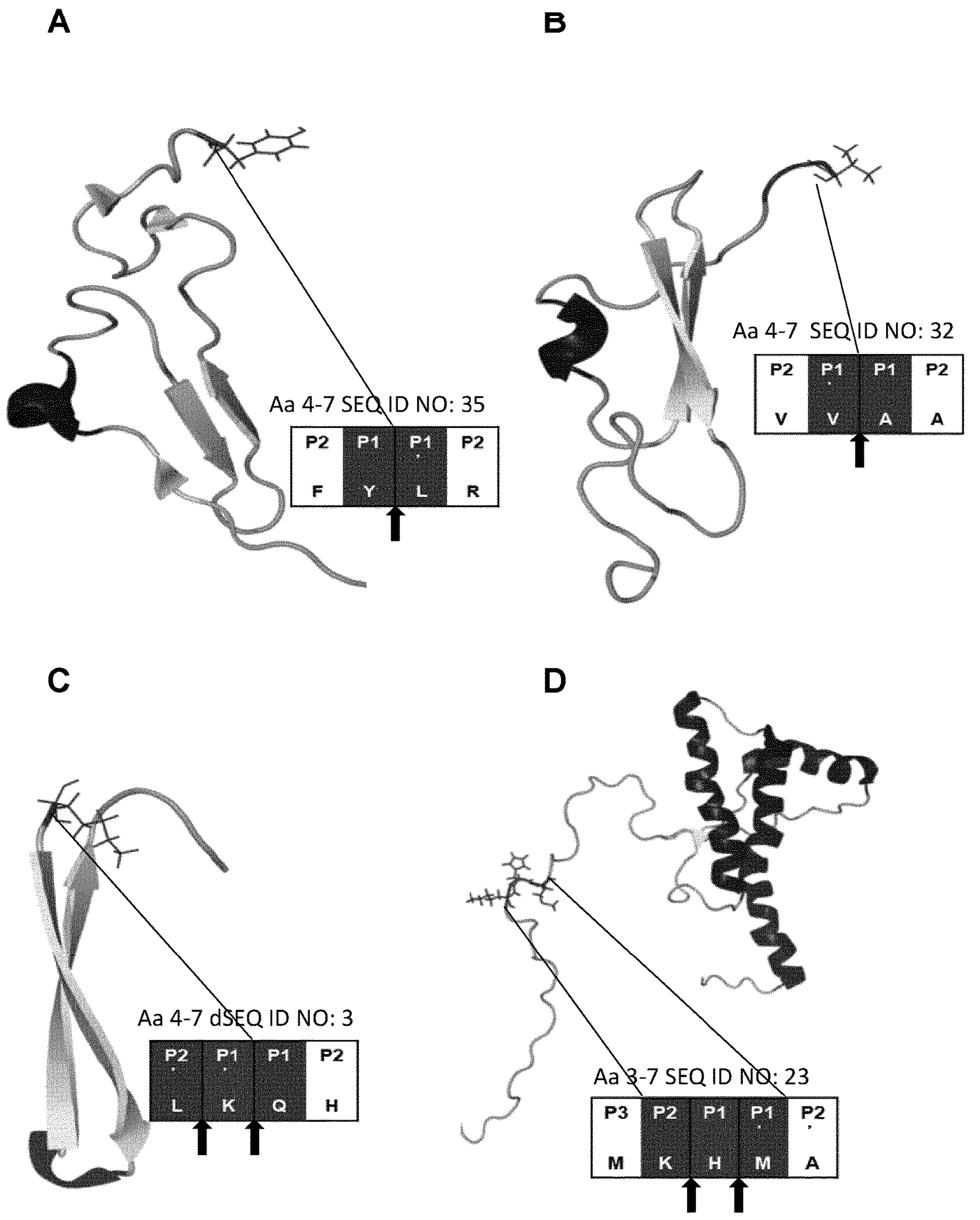

FIG. 4. 3D structure and sequence of ADAM10 cleavage sites.

A-D. 3D structures of ADAM10 substrates extracted from the "Protein Data Bank" database (PDB: www.rcsb.orq). Consensus sequences of the processing sites are boxed and highlighted in gray. A: human betacellulin-2 (PDB accession number 1IOX). B: Transforming growth factor alpha (TGF-alfa; PDB accession number: 1YUG). C: beta-amyloid (PDB accession number: 20TK). D: human prion mutant (PDB accession number 2KUN). In all cases the processing occurs in a loop portion of the protein.

E. E con. Consensus sequences at the processing sites of ADAM10 substrates. The table is from the Merops database (merops.sanger.ac.uk) integrated with additional data of processing sites in native proteins. Uniprot codes of processed proteins are listed. Amino acids flanking the processing site are indicated (SEQ ID NOs: 3-44). Corresponding residues/sites in the Trop-2 sequence are highlighted in light gray.

Figure 5:
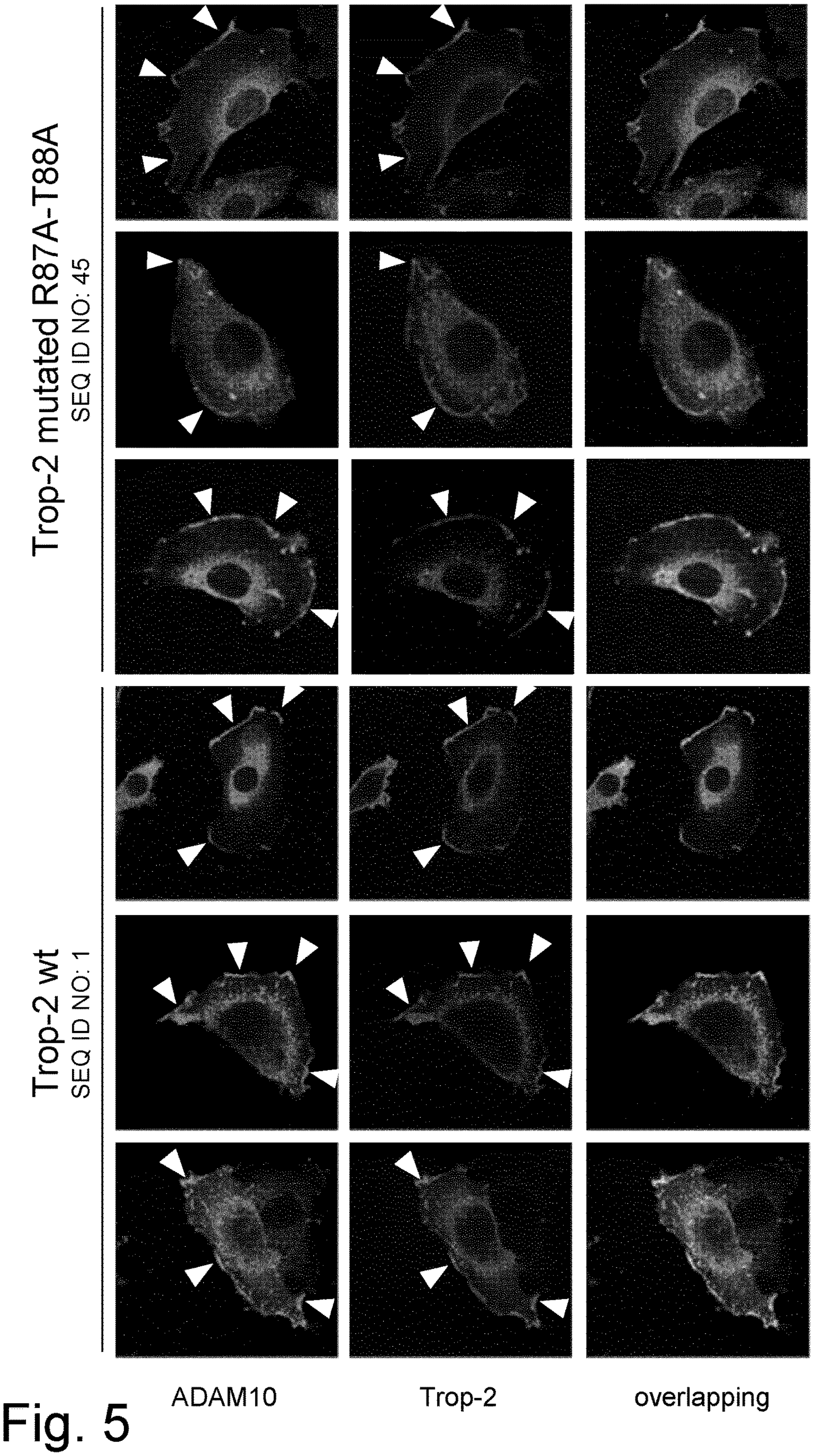

FIG. 5. Colocalization of ADAM10 with the wtTrop-2 and the processing-site Trop-2 mutant.

Immunofluorescence analysis of ADAM10 and Trop-2 localization. The two proteins colocalize at the cell membrane of MTE 4-14 cells transfected with wt (left) or mutated (right) Trop-2. White arrowheads indicate areas of colocalization. Full colocalization was shown in 72.2% of the cells (n=54), partial colocalization in 22.2% and no colocalization in 5.5%. wt: wild-type Trop-2 (SEQ ID NO: 1); R87A-T88A: processing site mutant (SEQ ID NO: 45), where R87 and T88 are substituted with two alanines (A).

FIG. 6. Identification of ADAM10 as a binding partner of Trop-2.

Trop-2 coimmunoprecipitated material was analysed by mass-spectrometry (MS) to identify Trop-2 binding partners. Four independent peptides (top panel, analysis output; SEQ ID NOs: 46-49) mapping on ADAM10 were identified (bottom panel, the MS peptides are highlighted in gray on the ADAM10 sequence: SEQ ID NO: 50), across multiple analytical procedures.

FIG. 7. Trop-2 processing by ADAM10.

ADAM 10 activity was inhibited in the MTE 4-14/Trop-2 transfectants by treatment with chemical inhibitors or mRNA silencing, and the effect on Trop-2 processing and on Trop-2-dependent cell growth was evaluated.

A. WB analysis following treatment with the broad-spectrum metalloprotease inhibitor GM6001 or with the specific ADAM10 inhibitor G1254023X or ADAM10 siRNA silencing, as indicated. Chemical inhibition of ADAM10 activity led to a reduction in the 40 kD processed Trop-2 band and a corresponding increase in the native form of Trop-2 (the bar graph shows the quantification by image analysis of the intensity of the WB bands corresponding to the native and processed forms of Trop-2 following treatment with G1254023X, compared with the control where the vehicle only was administered to the cells. ADAM10 inhibition upon specific siRNA treatment, as shown by the disappearance of the corresponding band (right, upper panel: ADAM10 WB) inhibited Trop-2 processing, as shown by the disappearance of the 40 and 10 kD bands (right, bottom panel: Trop-2 WB). T2-p: processed Trop-2; na: native form; pr: processed form.

B. (left) ADAM10 mRNA levels measured by RT-PCR 48 hours after transfection with specific siRNA or control siRNA (human CD133) in MTE 4-14 cells transfected with the empty vector, wtTrop-2 or the processing-resistant RA87-TA88 Trop-2 mutant. (right) mRNA levels of the MMP3, MMP9, Presenilin-2 (PSEN2) and ADAM10 metalloproteases, upon treatment with specific siRNAs or irrelevant control siRNAs. Bars: standard deviation.

C. In vitro growth curves of MTE 4-14 cells transfected with the empty vector, wtTrop-2 or R87A-T88A Trop-2 upon ADAM10 (upper graphs, black,), MMP9 (lower graphs, black,) or control (human CD133, gray), siRNA-mediated inhibition. Bars: SEM. The p value for the only significant difference (ANOVA analysis) is indicated. Stars indicate post-hoc Bonferroni's t test p values (*≤0.05, **≤0.001).

Figure 8:
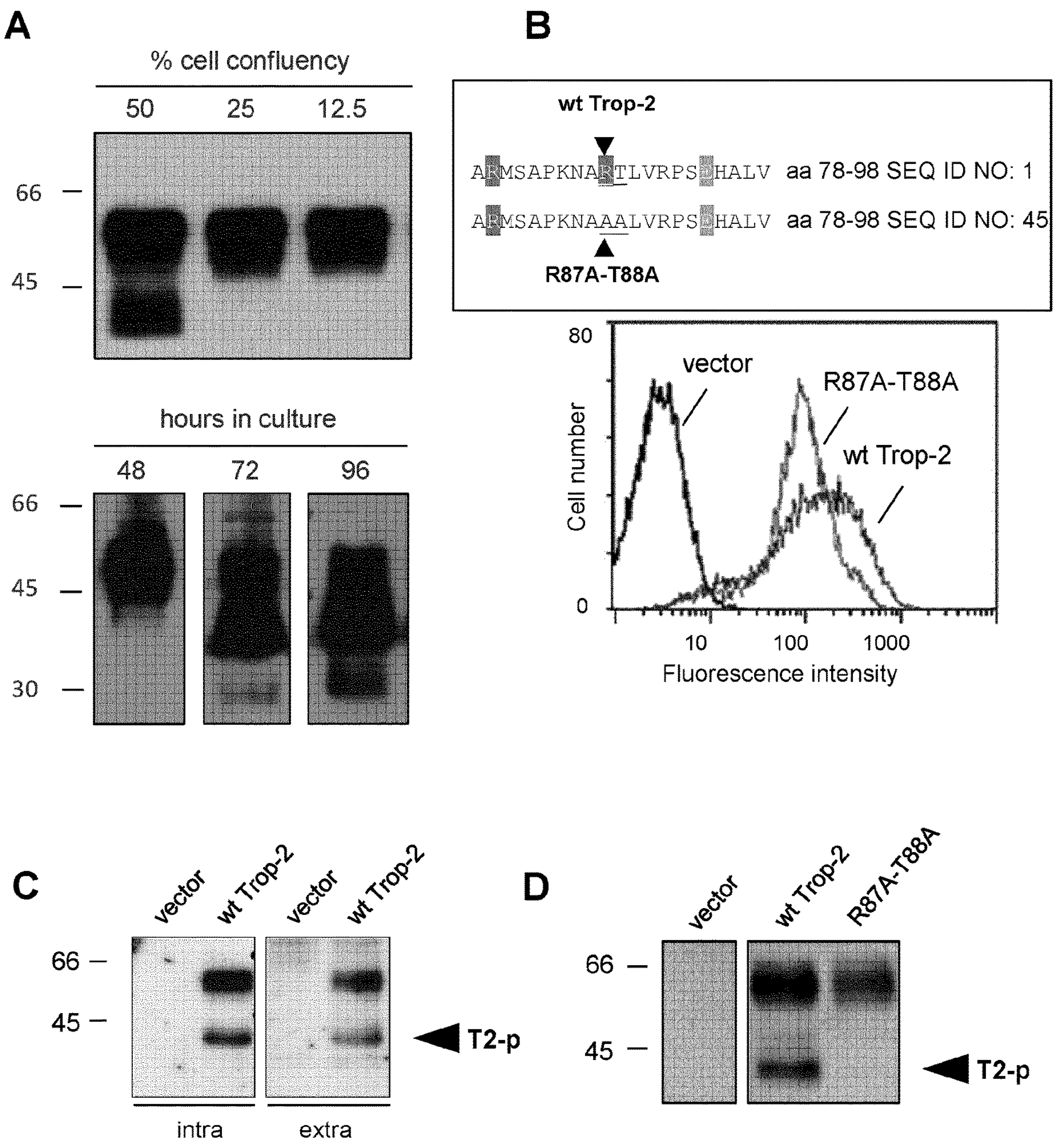
Figure 8:
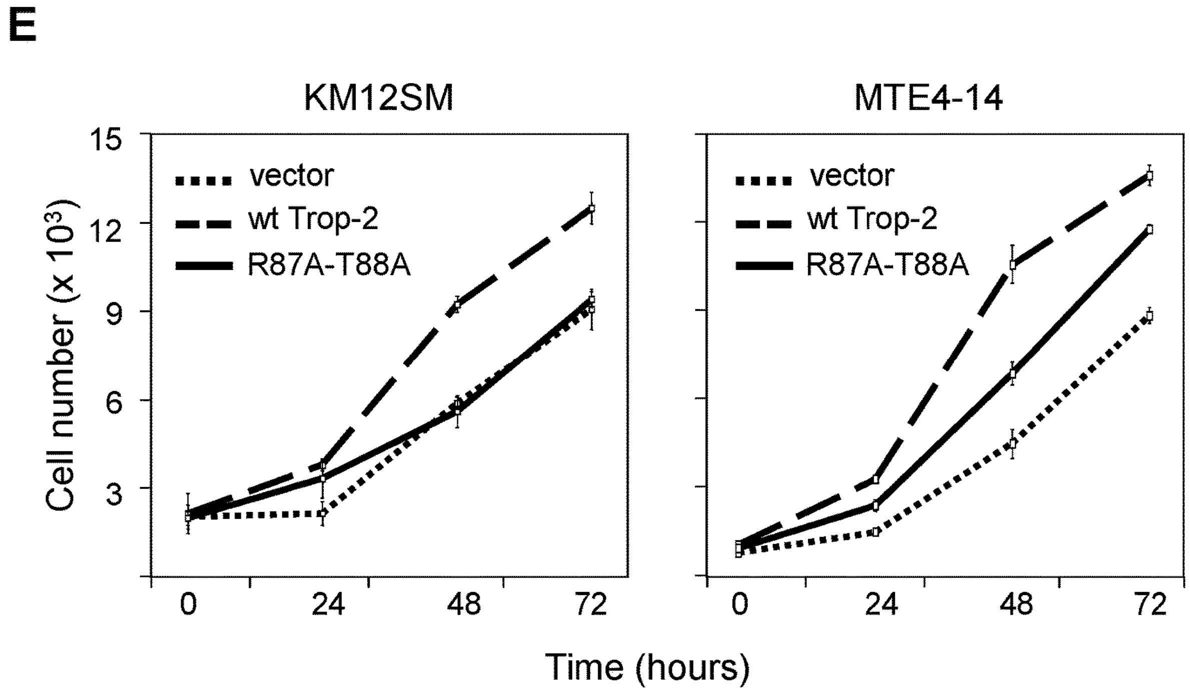

FIG. 8. The R87A-T88A mutation makes Trop-2 resistant to processing and inhibits in vitro growth.

A. WB analysis of MTE 4-14/Trop-2 transfectants growing in culture at different densities (upper panel) or for different lengths of time (lower panel). Trop-2 processing increases when cells come into contact in high confluency conditions (reached either by high density seeding or by prolonged time in culture).

B. Partial sequence of the R87A-T88A mutant (SEQ ID NO: 45) versus wild-type Trop-2 (SEQ ID NO: 1) (upper panel) and flow cytometry analysis of the corresponding MTE 4-14 transfectants with the T16 anti-Trop-2 mAb known in the art (lower panel).

C. WB analysis of MTE4-14/Trop-2 transfectants using polyclonal antibodies that bind either the extracellular domain (extra) or the cytoplasmic tail (intra). Processed Trop-2 (T2-p) retains the cytoplasmic tail.

D. WB analysis of KM12SM cells transfected with wtTrop-2 or with the R87A-T88A mutant. The RT-to-AA mutagenesis makes Trop-2 resistant to processing.

E. In vitro growth curves of KM12SM and MTE 4-14 cells transfected with wtTrop-2, the R87A-T88A mutant or the empty vector as a control, as indicated.

FIG. 9. Abolishing Trop-2 processing inhibits tumor growth and metastasis diffusion.

A. Tumor growth curves in vivo of L (left) and 293 (right) cells transfected with wtTrop-2 or with the R87A-T88A mutant. Bars: standard error of the mean (SEM).

B. Boxplot analysis of liver metastasis volume from in vivo assays using metastatic KM12SM colon cancer cells transfected with wtTrop-2 or with the R87A-T88A mutant.

C. Distribution curves of the volumes of Individual metastasis from the in vivo assays described above. Distributions were analyzed using the Mann-Whitney non-parametric statistical test. This showed a significant (p value=0.0436) reduction of volumes in the R87-T88 metastases (black solid line) versus wtTrop-2 (dashed line).

FIG. 10. Trop-2 processing in breast cancer.

A. WB analysis of Trop-2 in frozen samples from a consecutive breast cancer case series T2-p: processed Trop-2.

B. WB analysis of Trop-2 in frozen samples of normal breast tissues (8 individuals). T2-p marks the molecular weight corresponding to the processed Trop-2 band.

C. Image analysis distribution of the fraction of processed Trop-2 in the individual breast cancer samples from the WB shown in (A). Dashed lines: inflection points of the distribution curve.

FIG. 11. Trop-2 processing in tumor cells and in normal tissues from primates.

A. WB analysis of Trop-2 expression in cells from normal epidermis and in skin tumors (SCC: squamous cell carcinoma; KA: keratoacanthoma; BCC: basal cell carcinoma).

B. WB analysis of Trop-2 expression in normal tissues from rhesus monkey (*Macaca mulatta*): (top) 1: tongue; 2: urinary bladder; 3: heart; 4: salivary gland; 5: mammary gland; 6: skin; 7: kidney; (mid) 1: parotid gland; 2: oesophagus; 3: pancreas; 4: stomach; 5: thymus; (bottom) 1: brain; 2: eye; 3: thyroid; 4: parotid gland; 5: oesophagus; 6: lung; 7: liver; 8: pancreas.

C. WB analysis of in-vitro and in-vivo Trop-2 expression in cancer cells endogenously expressing Trop-2 (HT-29, colon; MCF-7, breast; OVCA: OVCA-432, ovary) or transfected with Trop-2-expressing vectors (MTE4-14, transformed thymus cells; HCT116, colon cancer; NS-0, myeloma; L, fibrosarcoma; 293, transformed embryonic kidney cells) in culture (left) or grown as tumors in nude mice (right). N: Untransfected cells; V: cells transfected with vector alone; T2: Trop-2-transfected cells; hiT2, IoT2: Trop-2-transfected NS-0 cells selected to express TROP2 at high or low levels, respectively. T2-p: processed Trop-2.

Figure 12:
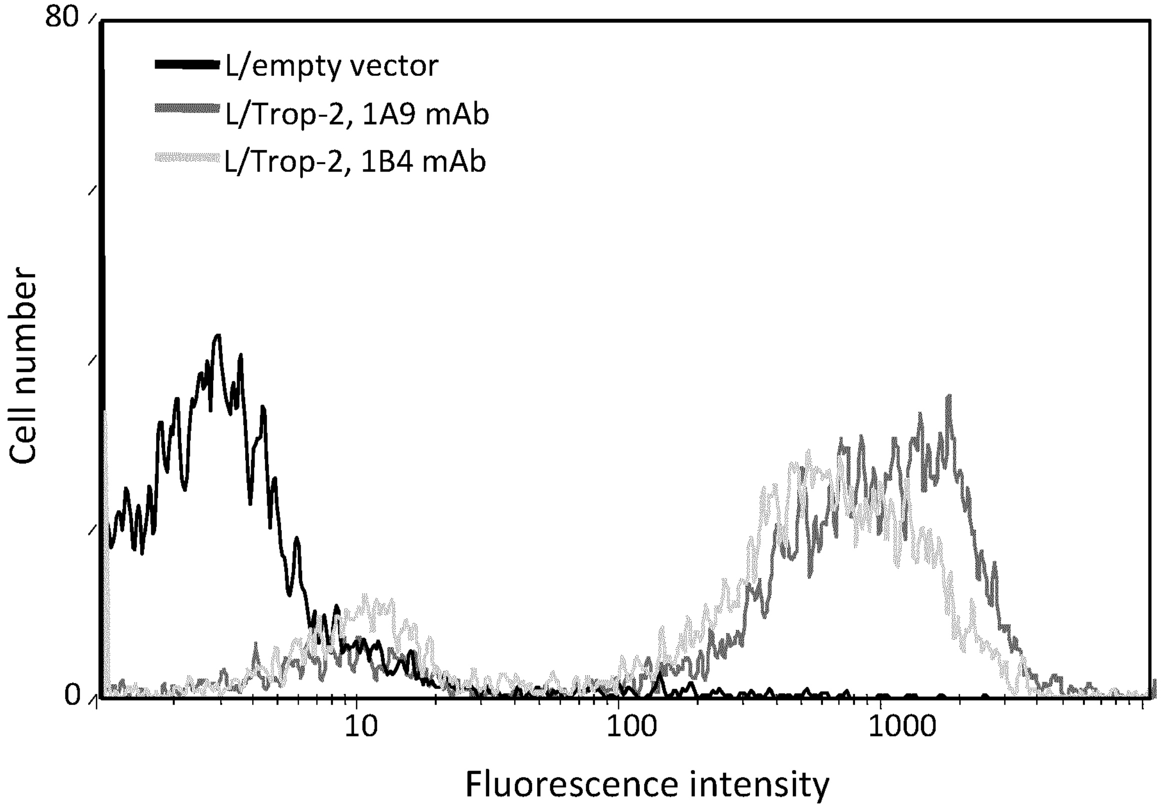

FIG. 12. Screening of mAbs according to the present invention: recognition of Trop-2.

Murine fibrosarcoma L cells transfected with wtTrop-2 or with the empty vector (control) were incubated with mAbs generated according to the present invention. Antibody binding was detected by means of incubation with a goat-anti-mouse antiserum conjugated with the Alexa488 fluorophore followed by flow citometry analysis. Two of the anti-Trop-2 mAbs that were identified are shown in this example.

FIG. 13. Screening of mAbs according to the present invention: differential recognition of the tumor-specific, fully processed Trop-2 versus the processing-resistant R87A-T88A mutant.

Human colon cancer KM12-SM cells transfected with wtTrop-2, or the processing-resistant R87A-T88A Trop-2 mutant (see FIG. 8D) were incubated with anti-Trop-2 mAbs generated according to the present invention and conjugated with Alexa488. Antibody binding was revealed by flow cytometry analysis. In this example one mAb is shown, of those that showed differential and specific recognition of the processed tumor-associated Trop-2. Solid arrow: fluorescence signal for the processed wtTrop-2; dashed arrow: decreased fluorescence signal for the processing-resistant R87A-T88A Trop-2 mutant. (Top panel) Overall Trop-2 expression levels were similar for the wt and the R87A-T88A mutant, as shown by staining with the T16 anti-Trop-2 mAb known in the art.

Figure 14:
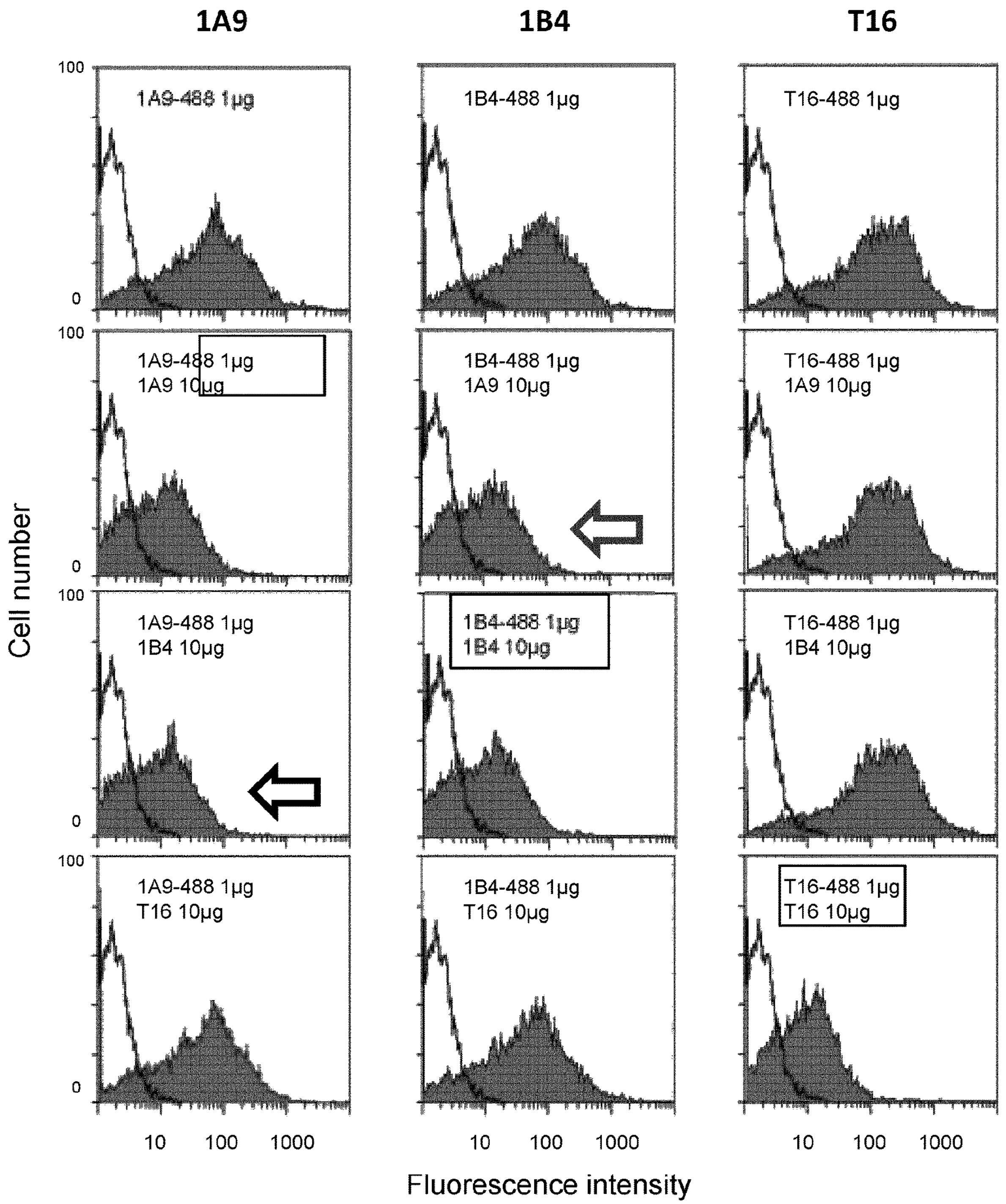

FIG. 14. Cross-competition assays between the anti-Trop-2 mAbs generated according to the present invention.

Human colon cancer KM12-SM cells transfected with wtTrop-2 were incubated with either (i) one of the anti-Trop-2 mAbs generated according to the present invention, which recognize the processed tumor-specific Trop-2 or (ii) with the T16 anti-Trop-2 mAb known in the art, conjugated with Alexa488, pre-mixed with a 10-times excess of the indicated unlabelled mAb. Antibody binding was revealed by flow cytometry analysis. Antibody competition for a shared epitope is revealed by the corresponding reduction in the fluorescence signal (arrows: 1A9 versus 1B4 and vice versa). Each mAb shows competition with itself, as expected.

Figure 15:
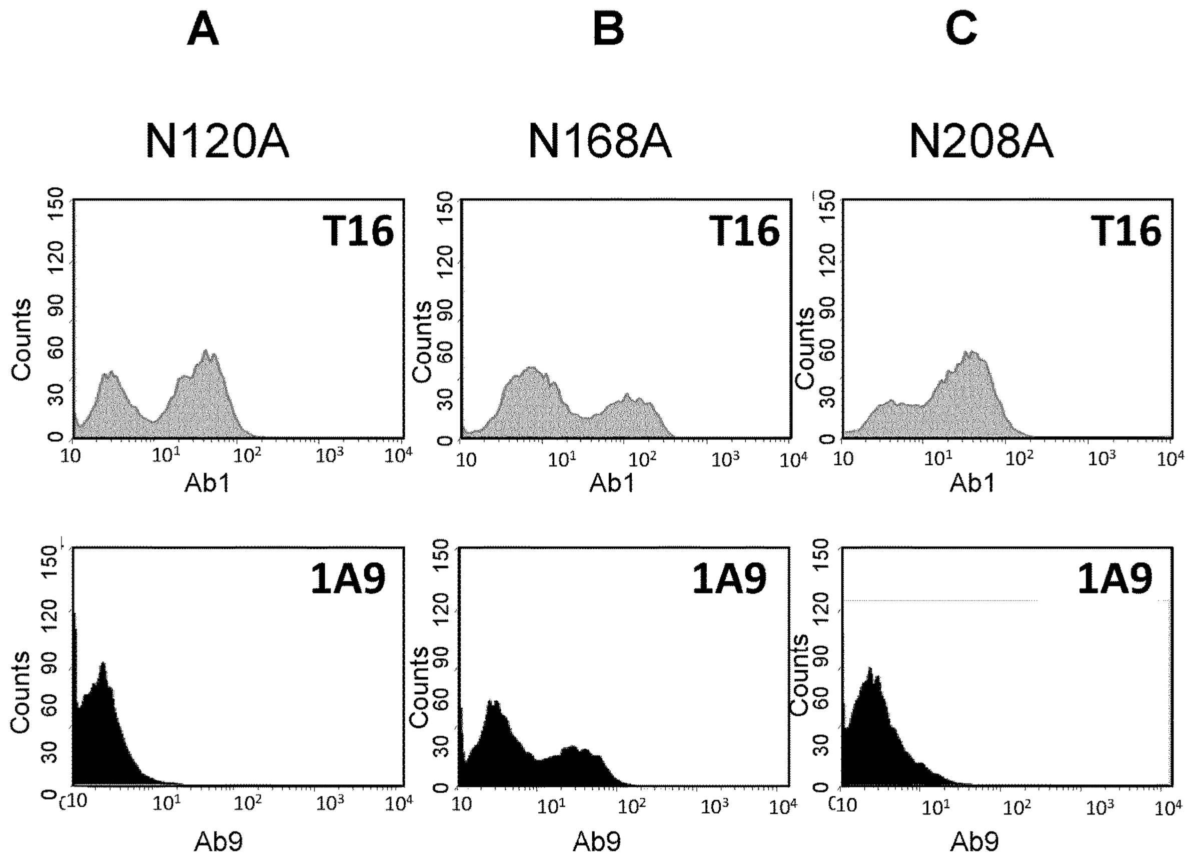

FIG. 15. Anti Trop-2 antibody binding to non-sequential glycosylation determinants in the Trop-2 extracellular domain.

Trop-2 glycosylation mutants (N substituted by A at the indicated positions) were analysed by flow cytometry with the benchmark T16 anti-Trop-2 MAb (top) or with the 1A9 anti-Trop-2 MAb (bottom) according to the present invention. Mutations of N to A at position 120 or 208 cause loss of binding by the 1A9 MAb (panel A, C), while a similar mutation at position 168 has no effect on 1A9 binding (panel B).

Figure 16:
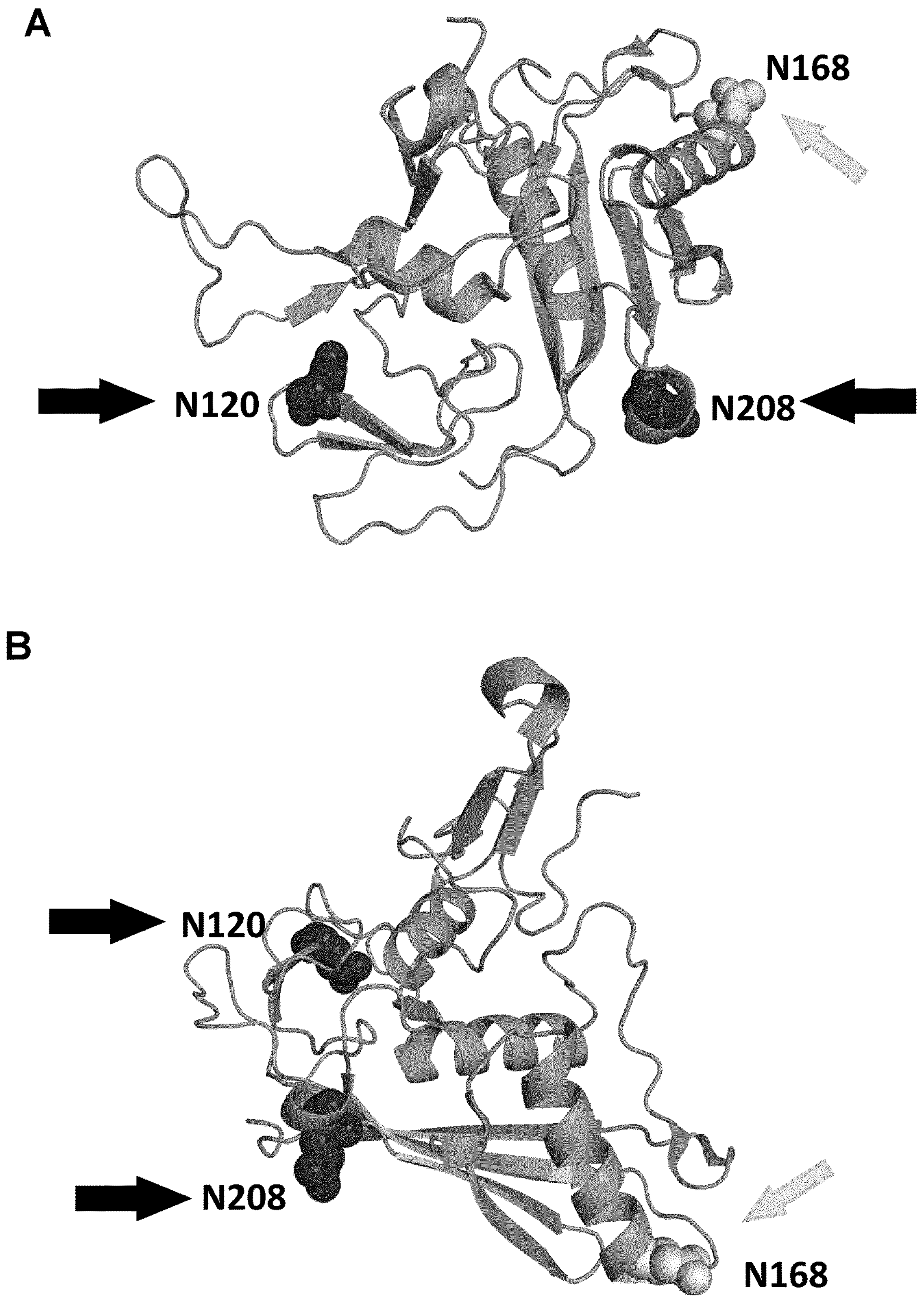

FIG. 16. Anti Trop-2 antibody binding surface on the Trop-2 3D structure.

Trop-2 3D structure with space-filling representation of N residues at 120, 168 and 208 positions. N residues bound by the 1A9 anti-Trop-2 MAb are in black (black arrows), while the N168 residue not involved in 1A9 binding is in light grey (grey arrow).

EXAMPLES

Materials and Methods

DNA Transfection

Cells were transfected with purified DNA in Lipofectamine 2000 or LTX (Invitrogen) according to the manufacturer instructions Flow Cytometry Cell staining for flow cytometry was performed with subtraction of cell autofluorescence and displacement of Alexa488- or FITC-stained cells in the red channel. Trop-2 transfectants were selected for expression levels comparable to those of endogenously expressing cancer cells. Reconstituted mixtures of L cells and Trop-2 transfectants were utilized for E1 mAb binding and competition studies of E1 with other anti-Trop-2 mAb, whereby cell mixtures were preincubated with 100× amounts of the indicated antibodies.

Immunofluorescence Microscopy

Cells grown on glass coverslips were fixed with 4% paraformaldehyde/PBS for 20 min. Staining was performed with the 162-46.2, T16, E1 anti-Trop-2, anti-ADAM10 and anti-CD9 antibodies, after permeabilization and blocking in 10% FBS, 0.1% saponin. Slides were viewed with an LSM-510 META (Zeiss) confocal microscope.

Confocal Time-Lapse Microscopy

Live cells cultured on glass slides were analyzed in Leibovitz's F15 culture medium without phenol red and bicarbonate, supplemented with 10% FBS, 100 IU/ml penicillin, 100 μg/ml streptomycin (Euroclone) and 2 mM N-acetylcysteine (Sigma), to reduce free-radical damage. Cells were viewed with an LSM-510 META (Zeiss) confocal microscope. Images were captured at 1 min intervals. Excitation of EGFP was at 488 nm; excitation mRFP was at 546 nm.

Breast Cancer Patient Case Series

Patients with breast cancer (N=453) with T1/T2 tumor diameter, without lymph node (Querzoli, Pedriali et al. 2006, Biganzoli, Pedriali et al. 2010) and distant metastases at the time of diagnosis were analyzed. Clinical and pathological status, tumor type, grading, expression of ERα, PgR, Ki-67-index were determined. Expression of Trop-2, uPA/PAI-1, MMP11, cathepsin D was assessed as indicated. The frozen material was lysed and processed as for Western blotting.

Cells

The human mammary MCF-7 cancer cell lines and the murine myeloma NS-0 cells were grown in RPMI 1640 medium supplemented with 10% fetal calf serum. The human 293 transformed kidney and murine L fibrosarcoma cell lines were maintained in DMEM supplemented with 10% fetal calf serum. Stable transfectants were propagated in complete medium supplemented with 100 μg/ml of G418.

Primate Samples

Frozen samples from various organs of Rhesus monkey (*Macaca mulatta*) were analyzed by WB to reveal Trop-2 expression and processing level in primate normal tissues. A rabbit polyclonal anti-human wtTrop-2 was utilized; this was shown to be highly specific for the monkey Trop-2. Tissue samples included: tongue; urinary bladder; heart; salivary gland; mammary gland; skin; kidney, parotid gland; esophagus; pancreas; stomach; thymus, brain; eye; thyroid; lung; liver.

In Vitro Cell Growth Assays

Cell transfectants were seeded at 1.5-3.0×$10^3$ cells/well in 96-well plates (five replica wells per data point). Cell numbers were quantified by staining with crystal violet. Cell numbers were normalized against a standard reference curve of two-fold serially diluted cell samples.

Antibodies

E1 mAb: Balb/c mice were immunized with Fe cells. Cell fusion and hybridoma cloning were carried out as known in the art. A screening for cell surface-reactive hybridomas was performed by immunohistochemistry on Fe cells and by flow cytometry on Trop-2 transfectants. Monoclonal antibodies from the E1 hybridoma were purified by affinity chromatography on Protein-A Sepharose and conjugated to fluorescein-isothiocyanate (FITC) or NHS-Alexa Fluor 488.

Rabbit polyclonal antibodies: Rabbit polyclonal anti Trop-2 antisera were generated by subcutaneous immunization with the recombinant extracellular domain of human Trop-2 synthesized in bacteria (El Sewedy, Fomaro et al. 1998), or with KLH-conjugated, N-ter biotinylated peptides corresponding to the cytoplasmic tail of human Trop-2. Anti Trop-2 polyclonal antibodies were purified by affinity-chromatography on recombinant Trop-2 conjugated to NHS-Sepharose (GE Healthcare) or biotinylated Trop-2 cytoplasmatic tails conjugated to Streptavidin-Agarose (Sigma-Aldrich). Purified antibodies were eluted with 0.2 M glycine pH 2.5.

Polyclonal antibodies known in the art: AF650 polyclonal goat anti-Trop-2 was purchased from R&D Systems (Minneapolis, MN, USA). Rabbit polyclonal anti-ADAM10 was purchased from Calbiochem (Merck Chemicals Ltd., Nottingham, UK); goat polyclonal anti-ADAM10 (sc-31853) and rat monoclonal anti-CD9 (sc-18869) were obtained from Santa Cruz (Santa Cruz Biotechnology, CA). Secondary Alexa Fluor (488, 546, and 633) conjugated antibodies were provided by Invitrogen.

Immunoprecipitation

Cells were washed with cold wash buffer (10 mM HEPES, 150 mM NaCl, 1 mM $CaCl_2$, 1 mM $MgCl_2$, pH 8) and lysed with 3 ml of lysis buffer (1% Triton, 0,1% SDS, 20 mM NaF, 1 mM $NaVO_4$, 2 mM PMSF, 5 μM Pepstatin, 5 μM Leupeptin). After centrifugation at 15,000 rpm for 5 min at 4° C., protein concentration of the supernatant was quantified with a Bradford protein assay and the supernatant was used for immunoprecipitation (IP). Four mg of lysate were incubated with T16-NHS Sepharose on a rotating wheel at 4° C. for 3 h. After centrifugation at 1,000 rpm, the resin was washed 3 times with PBS. T16-bound Trop-2/protein complexes were eluted 3 times with 150 μl of 0.1 M glycine buffer pH 2.5. Eluted solutions were immediately neutralized with TRIS 1 M pH 11.5.

Antigen Purification and Protein Sequencing

Trop-2 was purified by affinity chromatography over a Sepharose-E1 mAb column. Briefly, Fe cell monolayers were extensively washed in PBS and lysed in 20 mM TRIS-CI pH 7.4, 150 mM NaCl, 0.5% Triton X-100, 50 U/ml aprotinin, 1 mM AEBSF for 20 min at 4° C. The cell lysate was centrifuged at 1,500 g for 10 min; the supernatant was cleared by centrifugation at 12,000 g for 20 min and passed through a hydroxyapatite column (DNA-grade Bio-Gel HTP, Richmond, CA). The unbound fraction was loaded onto a Sepharose-E1 mAb column. Bound material was eluted with 0.1 M glycine pH 2.7, 0.1% Triton X-100. The eluate was immediately neutralized with 1 M TRIS pH 9, and eluted fractions were analyzed by SDS-PAGE on 4-18% gradient gels and Western blotting. Fractions containing the E1-immunoreactive material were pooled, concentrated, and transferred to a PVDF membrane. N-terminal sequences of the blotted protein samples were obtained by Edman degradation. The N-terminus of unprocessed Trop-2 appeared blocked/resistant to sequencing procedures.

Mass Spectrometry Analyses

Immunoprecipitated material was incubated at 37° C. with sequencing-grade porcine trypsin (Promega). A 1 ml aliquot of each peptide mixture was analyzed by MALDI Mass Spectrometry (MS) (www.york.ac.uk/depts/biol/tf/proteomics/). Positive-ion mass spectra were obtained using a Bruker Ultraflex III in reflectron mode, equipped with a Nd:YAG smart-beam laser. Identifications were obtained by MS-Fit web-application of ProteinProspector v5.7.3 (prospector.ucsf.edu/prospector/cgi-bin/msform.cgi?form=msfitstandard; UCSF). The peaks list by the mass spectrometer was used as input. We imposed as constant modification the carbamido-methylation, by reaction with iodoacetamide. Methionine oxidation, N-terminus acetylation, and transformation of peptide N-terminal Gln to pyroGlu were imposed as recognizable modifications. The mass tolerance was set at 100 ppm. Contaminant masses of the matrix α-cyano-4-hydroxycinnamic acid were excluded from analysis. Protein identifications were ranked on MOWSE score. The MOWSE score reported by MS-Fit is based on an updated scoring system (Pappin, Hojrup et al. 1993).

MS Identification of Proteolytic Cleavage Sites

To identify proteolytic processing sites of Trop-2, PMF-mass spectrometer-peak lists was analyzed by MS-Fit as above. To identify processing in vivo, spectra were scanned for peptide sequences that did not fit trypsin cleavage consensus sites. The mass tolerance was set at 20 or 50 ppm (50 ppm data are shown). Contaminant masses of matrix α-cyano-4-hydroxycinnamic acid were excluded from analysis.

Western Blotting

Western blotting was performed as described (El Sewedy, Fomaro et al. 1998). Tumors from experimental animals were rapidly frozen upon surgical removal and stored at −80° C. Frozen samples were quickly thawed and homogenized with a Dounce homogenizer. Cleared homogenates of tumors and cultured cell lysates were analyzed by SDS-PAGE and transferred to nitrocellulose filters. Filters were hybridized with anti-human Trop-2 (affinity-purified polyclonal rabbit antiserum) or anti-ADAM10 antibodies. Antibody binding was revealed by goat anti-rabbit or rabbit anti-goat peroxidase (Calbiochem, La Jolla, CA) via chemiluminescence (ECL; Amersham, Aylesbury, UK) (El Sewedy, Fomaro et al. 1998).

Plasmids

The pBJI-neo vector was provided by Dr. M. Davis. The Bluescript vector was obtained from Stratagene (La Jolla, CA). The pcDNA3 expression vector was obtained from Invitrogen (Gröningen, The Netherlands). The pEYFP-N1 was obtained by Clontech (Palo Alto, CA).

TROP2 Constructs

A 970 bp full-length E1/TROP2 cDNA from Fe cells was isolated by RT-PCR, using the Titan System kit from Boehringer (Mannheim, Germany) and total Fe cell RNA as template. The amplified band was digested with Bam HI and Eco RI and subcloned in the corresponding sites of the pcDNA3 expression vector using the following primers:

```
F:
                                    (SEQ ID NO: 51)
5'-CTCGGATCCATGGCTCGGGGCCCCGGCCTC-3'

R:
                                    (SEQ ID NO: 52)
5'-CTCGAATTCCAAGCTCGGTTCCTTTCTCAA-3'.
```

A pEYFP-derived vector devoid of the coding sequence of the EYFP fluorescent protein (pΔEYFP vector) was used to express Trop-2 in mammalian cells. Cells transfected with pΔEYFP are indicated as "control", or "vector-alone" cells. Wild-type TROP2 was obtained by PCR from the original full length genomic TROP2 clone, and inserted in the vector at the XhoI/KpnI sites, using the following primers:

```
F:
                                    (SEQ ID NO: 53)
5'-GCGATTctcgagTCCGGTCCGCGTTCC-3' (the XhoI site
is underlined)

R:
                                    (SEQ ID NO: 54)
5'-GCGCCggtaccAAGCTCGGTTCCTTTC-3' (the KpnI site
is underlined)
```

R87A-T88A Trop-2 mutant was generated by site-specific mutagenesis of the Trop-2 processing site with the Quikchange® Site-directed mutagenesis kit (Stratagene) following the instruction of the manufacturer, using the following primers:

```
F:
                                    (SEQ ID NO: 55)
5'-AGCGCCCCCAAGAACGCCGCCGCGCTGGTGCGGCCG-3'

R:
                                    (SEQ ID NO: 56)
5'-CGGCCGCACCAGCGCGGCGGCGTTCTTGGGGGCGCT-3'
```

The mutagenized coding region was entirely sequenced, to verify the absence of any Taq polymerase-induced mutations.

ADAM10 Inhibitors

Cells were treated with ADAM10 inhibitors for 24 hours at the minimum concentration found to be effective in inhibiting Trop-2 cleavage, then assayed as indicated. The GM6001 metalloprotease family inhibitor (Calbiochem) was dissolved in DMSO and used at 6.5-13 μM for 24 hours; up to 50 μM GM6001 were found effective. The G1254023X selective ADAM10 inhibitor, dissolved in DMSO, was kindly provided by Dr. A. Ludwig. Cells received two doses (10 μM) every 24 hours for 48 hours; up to 20 μM G1254023X were found effective. Control cells received vehicle alone.

ADAM10 siRNA

Complementary strategies were utilized for siRNA design. Briefly, Tuschl' criteria were applied, i.e. position in the mRNA, GC content, base composition and flanking sequences (Elbashir, Harborth et al. 2001). Invitrogen (maidesigner.invitrogen.com/maiexpress/) provides a proprietary algorithm that performs a statistical analysis of the target sequence, based on sequence composition, nucleotide content and thermodynamic properties, and compares candidates with validated siRNA sequences. The Whitehead Institute web site (jura.wi.mit.edu/bioc/siRNAext/) combines Tuschl' criteria with predictions of binding energies for both sense and antisense siRNAs and with BLAST filtering of cross-hybridizing sequences. The Sonnhammer procedure (sonnhammer.cgb.ki.se/siSearch/) performs data mining (siSearch) on validated siRNA databanks, using motif rules and energy parameters. siRNA were synthesized that were identified by more than one method or considered optimal by any of the procedures above. Annealed oligos were subcloned into the pSUPER vector, kindly provided by Dr. R. Bernard (Brummelkamp, Bernards et al. 2002), under the control of the RNA polymerase III H1 gene promoter. siRNA expression constructs were transiently transfected MTE 4-14 transfectants, and cell growth was measured. siRNA-targeted transcript levels were quantified by real-time PCR. Negative control siRNAs directed towards irrelevant targets were used; these were chosen after extensive testing for lack of off-target influence on cell growth.

siRNA targeting murine ADAM10 (NM_007399.3, nt 292-309) (Schramme, Abdel-Bakky et al. 2008)

```
F:
                                        (SEQ ID NO: 57)
5'-gatccccAGACATTATGAAGGATTATttcaagagaATAATCCTTCA
TAATGTCTtttttggaaa-3'

R:
                                        (SEQ ID NO: 58)
5'-agcttttccaaaaaAGACATTATGAAGGATTATtctcttgaaATAA
TCCTTCATAATGTCTggg-3'.

siRNA targeting murine MMP9 (NM_013599, nt
1780-1798)
F:
                                        (SEQ ID NO: 59)
5'-gatccccCCGCAGACCAAGAGGGTTTttcaagagaAAACCCTCTTG
GTCTGCGGtttttggaaa-3'

R:
                                        (SEQ ID NO: 60)
5'-agcttttccaaaaaCCGCAGACCAAGAGGGTTTtctcttgaaAAAC
CCTCTTGGTCTGCGGggg-3'

Negative control siRNAs for murine cells
targeting human CD133 (NM_006017.1, nt 1061-1079)
F:
                                        (SEQ ID NO: 61)
5'-gatccccCTTGACAACGTTAATAACGttcaagagaCGTTATTAACG
TTGTCAAGtttttggaaa-3'

R:
                                        (SEQ ID NO: 62)
5'agcttttccaaaaaCTTGACAACGTTAATAACGtctcttgaaCG
TTATTAACGTTGTCAAGgg-3'

Negative control siRNAs for murine cells
targeting human CD316 (NM_052868.2, nt 801-819)
F:
                                        (SEQ ID NO: 63)
5'gatccccTGCAGGAAGTGGTGGGAATttcaagagaATTCCCACC
ACTTCCTGCAtttttggaaa-3'

R:
                                        (SEQ ID NO: 64)
5'agcttttccaaaaaTGCAGGAAGTGGTGGGAATtctcttgaaAT
TCCCACCACTTCCTGCAggg-3'
```

Quantitative RT-PCR

One μg of total RNA was reverse transcribed with the ImProm-II Reverse Transcriptase (Promega) according to standard protocols. Quantitative RT-PCR was performed using an ABI-PRISM 7900HT Sequence Detection System and Power SYBR® Green PCR Master Mix (PE Applied Biosystems, Foster City, CA) according to the manufacturer instructions, using the listed primers:

```
Murine ADAM10 F:
                                        (SEQ ID NO: 65)
5'-AGCAACATCTGGGGACAAAC-3'

Murine ADAM10 R:
                                        (SEQ ID NO: 66)
5'-TTGCACTGGTCACTGTAGCC-3'

Murine MMP9 F:
                                        (SEQ ID NO: 67)
5'-GTGCGACCACATCGAACTT-3'

Murine MMP9 R:
                                        (SEQ ID NO: 68)
5'-GGATGCCGTCTATGTCGTCT-3'

Murine B2M F:
                                        (SEQ ID NO: 69)
5'-GAGCCCAAGACCGTCTACTG-3'

Murine B2M R:
                                        (SEQ ID NO: 70)
5'-AAAGAAGGTGATGTGTACATTGCT-3'
```

Each sample was assayed in triplicate. The 2-ΔΔCT method was used to calculate relative changes in gene expression. A more accurate base of 1.834 was used (Guerra, Trerotola et al. 2008), as 1.1 cycles are required to double the amplified material. The β2-microglobulin (B2M) housekeeping gene was used as an internal control. For set-up curves, ΔCT (CT, target gene—CT, GAPDH) were calculated for each cDNA dilution. The data were fit using least-squares linear regression analysis. As relative amplification efficiency was invariant over the range of RNA amounts used (Zanna, Trerotola et al. 2007, Guerra, Trerotola et al. 2008), amplification curves were used to calculate cross-over point values for siRNA-treated samples. Each sample was routinely assessed for genomic DNA contamination by using non-retrotranscribed RNA isolates as templates for PCR reactions.

Sequence Analysis

Subcloned PCR bands were sequenced to confirm the correctness of the construct and the absence of PCR-induced mutations. DNA and protein sequences were analyzed using GCG and EMBOSS (www.uk.embnet.org/Software/EMBOSS/) programs. Analysis of ADAM10 substrates was performed through the Merops database (merops.sanger-.ac.uk/cgi-bin/protsearch.pl). The interrogation output was cross-checked with additional, updated published data on native-protein cleavage-sites.

3D Structure Analysis and Modeling

The structure of the thyroglobulin domain of the p41 isoform of the invariant chain of MHC class II (PDB code 1ICF, chain 1) (Guncar, Pungercic et al. 1999) was used as a template for the homology-modeling of the Trop-2 thyroglobulin region. The Trop-2 and p41 thyroglobulin domains (aa 71-145 di SEQ ID NO: 1 and aa 211-271 di NP_001020330.1 respectively) were aligned using GAP and NEEDLE software. Alignments were manually refined in regions with lower conservation, using conserved cysteines and secondary structures as anchor sites. A short α-helix around the first cysteine of the Trop-2 thyroglobulin domain was concordantly predicted by secondary-structure prediction programs (PHDsec at cubic.bioc.columbia.edu/predictprotein/; jpred2 at jura.ebi.ac.uk:8888/; 3D-pssm atwww.bmm.icnet.uk/~3dpssm/), in good correspondence to that of p41. A model of the tertiary structure of the Trop-2 thyroglobulin domain was built using the programs MODELLER-4 and WHATIF (bioslave.uio.no/Programs/MVL/index.php3). Similar results were obtained with the two software and only the model generated by MODELLER was further analyzed. The stereochemical properties of the resulting models were assessed with the program PROCHECK. The graphic representations of the MODELLER outputs were prepared with the MOLMOL, Swiss-PdbViewer (www.expasy.ch/swissmod/SWISS-MODEL.html), RasMol (www.umass.edu/microbio/rasmol/) and Raster3D (asdp.bnl.gov/asda/LSD/Modeling/Raster3D.html) programs. Modelling and model evaluation were performed on a Silicon Graphics Octane r12000 workstation. PDB files of ADAM10-cleaved proteins were retrieved from the PDB databank (www.rcsb.org/pdb/home/home.do), and analyzed as described above. Structure images were generated with PyMol (www.pymol.org/).

Experimental Tumors and Metastases

Transformed cell lines and TROP2-transfectants were injected subcutaneously (SC) in 8-week-old female athymic Crl:CD1-Foxn1nu mice (Charles River Laboratories). SC tumor growth was quantified as described (Rossi, Di Lena et al. 2008). To assess metastatic diffusion, KM12SM colon cancer cell (Morikawa, Walker et al. 1988) transfectants were injected in the spleen of 8-week old female athymic Crl:CD1-Foxn1nu mice. After 4 weeks mice were euthanized; tumor growth and diffusion to the liver or other organs were determined. All autoptic samples underwent microscopy histopathology analysis to detect minimal tumors and metastatic burdens.

Procedures involving animals and their care were conducted in compliance with institutional guidelines, national laws and international protocols (D.L.No. 116, G.U., Suppl. 40, Feb. 18, 1992; No. 8, G.U., July, 1994; UKCCCR Guidelines for the Welfare of Animals in Experimental Neoplasia; EEC Council Directive 86/609, OJL358. 1, Dec. 12, 1987; Guide for the Care and Use of Laboratory Animals, United States National Research Council, 1996).

Results

Identification of an Immunodominant Trop-2 Epitope

The E1 antibody generated as described above and selected for the recognition of native Trop-2 in tumor cells was compared to anti-Trop-2 mAbs known in the art by flow cytometry competition experiments (FIG. 2). Efficient competition with E1, as shown by the disappearance of specific staining of Trop-2 expressing cells, was observed for the 162-46.2, T16, and RS7-3G11 (from which the humanized therapeutic IMMU132 is derived (Bardia, Mayer et al. 2019)) anti-Trop-2 mAbs. This indicates the existence of an immunodominant Trop-2 epitope that is shared by multiple mAbs obtained from independent immunization procedures, and present in tumor as well as normal tissues (Fradet, Cordon-Cardo et al. 1984). Mapping using Trop-2 deletion mutants identified this immunodominant epitope in the extracellular region spanning D146-R178 (Ikeda, Yamaguchi et al. 2015), poised between the globular and the stem regions.

Identification of Processed Forms of Trop-2 in Tumors

Trop-2 was immunoprecipitated from ovarian carcinoma cells using the E1 antibody, purified by affinity chromatography on an E1-NHS-Sepharose mAb column as described (purity>95%, as indicated by WB analysis, FIG. 2, B) and sequenced at the N-terminus by Edman degradation. Sequencing identified a form of Trop-2 that starts with threonine at position 88 (T88) (SEQ ID NO: 71), most likely originating from a processing of the complete molecule at a cleavage site between arginine 87 (R87) and threonine 88 (T88) in the thyroglobulin domain (FIG. 2). This result was then confirmed by MS analysis of the purified Trop-2, which identified 4 independent peptides mapping on the processed form. The alignment of the Trop-2 sequence with that of the Trop-1 paralogue highlights the correspondence between the Trop-2 R87-T88 and the Trop-1 R80-R81 processing sites (Schön, Schön et al. 1993). Other authors have independently identified the existence of multiple forms of processing of the Trop-2 molecule, at the same R87-T88 site T88 (Kamble, Rane et al. 2020, Wu, Lu et al. 2020) or at the A187-V188 and subsequently G285-V286 sites, in a two-stage activation by TACE and presenilin that leads to the release and translocation into the nucleus of the Trop-2 cytoplasmic tail (Stoyanova, Goldstein et al. 2012).

3D Modelling of the Thyroglobulin Domain of Trop-2

The authors of the present invention generated a 3D model of the thyroglobulin domain of Trop-2 (FIG. 3), using sequence homology modelling on the 3D structure of the MHC class II p41 invariant chain (Guncar, Pungercic et al. 1999) as a template, as described above. This allowed the identification of 3 distinct loops with different spatial orientation, and the mapping of the R87-T88 processing site in the first loop. Based on this model, the cleavage at this position is expected to generate a two-chain molecule, in which a ~10 kDa fragment (SEQ ID NO: 72) is bound to the ~40 kDa membrane-bound segment (SEQ ID NO: 71) by a single disulphide bridge between Cys73 and Cys108 (aa numbering refers to the full length Trop-2 molecule with SEQ ID NO: 1). This prediction is confirmed by Trop-2 SDS-PAGE where a ~10 kDa decrease in molecular weight is observed under reducing with respect to non-reducing conditions (FIG. 2). The model also indicates that processing at R87-T88 makes the smaller subunit free to swivel over the Trop-2 backbone, and this is predicted to have a major impact on Trop-2 structure, function, and molecular interactions.

Identification of the Effector Molecule of Trop-2 Processing

It is known in the art that clusters of proteases act sequentially for the processing of surface molecules, thus activating signalling pathways that are involved in metastatic diffusion. Cancer-related protease families such as uPA/PAI-1, MMP11 and cathepsin D have been evaluated in a series of breast cancer patients, but none were found to be directly related to Trop-2 processing. Other metalloproteases involved in cell adhesion mechanisms and expressed in cancer were then investigated. Among these, the ADAM10 metalloprotease has been shown to cleave target molecules within loops that have structural characteristics like those identified in Trop-2 (FIG. 4). ADAM10 is found upregulated in gastric (Wang, Ye et al. 2011), hepatic (Bai, Nasser et al. 2009), colorectal (Gavert, Conacci-Sorrell et al. 2005), uterine, ovarian (Fogel, Gutwein et al. 2003) and oral squamous-cell (Ko, Lin et al. 2007) carcinomas, similarly to what was found for Trop-2 (Trerotola, Cantanelli et al. 2013). Moreover, analysis of the processing site in R87-T88 showed characteristics of ADAM10 target sites (SEQ ID NOs: 3-44) (FIG. 4). In agreement with these observations, ADAM10 was shown to colocalize with Trop-2 at the cell membrane (FIG. 5). MS analysis of immunoprecipitated Trop-2 identified four independent peptides (SEQ ID NOs: 46-49) mapping on the ADAM10 sequence (SEQ ID NO: 50), and thus formally demonstrated the physical interaction between ADAM10 and Trop-2 (FIG. 6).

To confirm that ADAM10 is indeed responsible for the processing of Trop-2 described above, transfected cells expressing Trop-2 were treated with an inhibitor of metalloprotease enzymatic activity (GM6001) or specific for ADAM10 (G1254023X) or subjected to ADAM10 gene expression silencing by specific siRNAs (FIG. 7). In all cases, inhibition of ADAM10 caused a corresponding reduction in Trop-2 processing. Trop-2 processing was virtually abolished following ADAM10 silencing. Hence these data confirm the role of ADAM10 as an effector molecule of Trop-2 processing.

Furthermore, it has been shown that R87-T88-processed Trop-2 is recognized by polyclonal antibodies directed against the cytoplasmic tail (FIG. 8, C), indicating that the cytoplasmic tail is retained as an integral part of the processed molecule. The processing here described is therefore different and independent from that known in the art which is performed by TACE and presenilins (Stoyanova, Goldstein et al. 2012).

Pro-Tumorigenic and Pro-Metastatic Role of Trop-2 Processing

To investigate the functional role of Trop-2 processing, a mutated version of Trop-2 was created in which the two amino acids flanking the processing site were replaced with two alanines (SEQ ID NO: 45). WB analysis showed that this R87A-T88A mutant is resistant to processing (FIG. 8, D), and in vitro growth assays showed that the unprocessed Trop-2 mutant loses the ability to stimulate cell proliferation (FIG. 8, E). In vitro proliferation assays of transfectants expressing wtTrop-2 or the R87A-T88A mutant treated with siRNA specific for ADAM10 or inactive as controls showed that inhibition of ADAM10 overrides Trop-2 dependent growth stimulus in wtTrop-2 transfectants, while it has no effect on R87A-T88A or empty vector transfectants (FIG. 7, C). wtTrop-2 transfectants treated with siRNA specific for ADAM10 grow identically to R87A-T88A processing-resistant transfectants. Control siRNAs targeting MMP9 metalloprotease has no effect on cell proliferation (FIG. 7, C).

In vivo tumor growth and metastatic spread assays were also performed, in which colon cancer cells transfected with wtTrop-2 or with the R87A-T88A processing-resistant mutant were injected in nude mice either subcutaneously (tumor growth model) or in the spleen (liver metastatic spread model) (FIG. 9). In both models, the inactivation of the Trop-2 processing site by R87A-T88A mutagenesis abolished the Trop-2 dependent stimulation of tumor growth and metastasis.

Taken together these data show that processing by ADAM10 is necessary for Trop-2 to stimulate tumor growth and metastatic spread.

Trop-2 Processing is Found in Tumors and Absent in Normal Tissues

Trop-2 processing as described above has been detected in cell lines that were either transformed or tumor-derived. To better define how widespread this processing is in tumors, a WB analysis of a series of breast cancer patients was performed (FIG. 10). This analysis showed that 100% of the tumors had processed Trop-2 molecules, over one-half of them to high extents. Conversely, normal tissues analyzed in parallel showed complete absence of Trop-2 processing (FIG. 10). A similar analysis was extended to skin tumor samples, compared to normal epidermis (in which Trop-2 is expressed at high levels), and to a panel of tumor cell lines of different origin with endogenous Trop-2 expression (MCF-7, breast cancer; OVCA: OVCA-432, ovarian cancer; HT-29, colon cancer) or Trop-2 transfectants (NS-0, myeloma; 293, transformed kidney, L, fibrosarcoma, MTE 4-14, thymus transformed, HCT116, colon cancer) (FIG. 11). In most transformed cells (skin, ovarian, breast and colon cancer; transfected carcinoma, myeloma and fibrosarcoma cells) Trop-2 was found to be processed, while the normal epidermis showed no processing.

The Trop-2 sequence in primates is very similar to that of human Trop-2. Rhesus monkey (*Macaca mulatta*) Trop-2 (SEQ ID NO: 73) has 98.1% homology with human Trop-2, and perfect conservation of the processing sequence. An extensive panel of normal Rhesus monkey tissues was subjected to WB analysis for Trop-2 (FIG. 11), and in this case no processing was detected.

Therefore, Trop-2 processing by ADAM10 occurs specifically in tumors.

Production and Screening Procedures to Obtain mAbs that Recognize the Tumor-Specific Processed Trop-2

Trop-2-targeted analytical and therapeutic approaches known in the art have relied on anti-Trop-2 mAbs that recognize a single immunodominant epitope, poised between the globular and the stem regions, which is accessible and recognized in all Trop-2 expressing cells. In the present invention, novel procedures for the generation and selection of new mAbs against different Trop-2 epitopes have been developed and successfully applied, with the aim of obtaining anti-Trop-2 mAbs able to recognize and bind with high affinity processed forms of the target molecule with specific and differential expression in tumor cells.

To maximize the recognition heterogeneity of epitopes corresponding to regions of the target molecule with distinct structural and functional characteristics, an immunogen was used comprising both the entire extracellular portion (amino acids 31-274 of SEQ ID NO: 1) and single domains of the Trop-2 molecule (globular domain: amino acids 31-145 of SEQ ID NO: 1; “stem”: amino acids 146-274 of SEQ ID NO: 1). These were produced in their native folding in human 293 transformed kidney epithelial cells and MCF-7 breast adenocarcinoma, and murine L fibrosarcoma and NS-0 myeloma, in insect Sf9 and yeast cells. Expression vectors for production were generated using PCR amplification of Trop-2 coding sequences fused to tags for purification or immunogenicity enhancement. The PCR fragments were subcloned in the vectors described above and expressed in the corresponding hosts. The Trop-2 proteins were purified by affinity chromatography. BALB/c mice were subjected to multiple immunization cycles with the immunogen described above, following best procedures known in the art. Splenocytes from immunized mice were fused to Sp2/0 or NS-0 myeloma cells and corresponding hybridomas were obtained, according to the methods known in the art. The antibodies produced by the hybridomas thus obtained were screened for specific and differential reactivity towards the processed Trop-2 that is expressed by tumor cells. In one phase of the screening, the antibody ability to specifically bind Trop-2 was measured. An example is shown in FIG. 12, where flow cytometry analysis is applied to L cells transfected with TROP2 or with the empty vector (negative control): the fluorescence profiles are shown for two new mAbs (1A9 and 1B4), which bind Trop-2 with high efficiency and do not bind the negative control. In another phase of the screening, the antibody ability was measured to recognize and bind with high affinity only the tumor-specific processed form of Trop-2, and not the unprocessed Trop-2 found in normal tissues. An example is shown in FIG. 13, where flow cytometry analysis is applied to KM12SM transfectants expressing the processed wtTrop-2 (SEQ ID NO: 1) or the R87A-T88A processing-resistant mutant (SEQ ID NO: 45) (corresponding WB analyses of these transfectants are shown in FIG. 8, D), and control KM12SM cells transfected with the empty vector the fluorescence profile of the 1A9 mAb is shown, which is in able to bind with high efficiency only Trop-2 in its processed form, and not the processing-resistant mutant. Expression levels of wt and mutant Trop-2 in the corresponding transfectants are identical, as demonstrated by a parallel analysis using the T16 anti-Trop-2 antibody known in art (FIG. 13, top left panel). Flow cytometry cross-competition experiments between 1A9, 1B4 and T16 mAbs on KM12SM/wtTrop-2 and KM12SM/vector transfectants demonstrated that 1A9 and 1B4 blocked each other's binding, thus indicating recognition of the same epitope. On the contrary, there is no competition of 1A9 and 1B4 against T16, demonstrating how the procedures here described have effectively allowed to obtain mAbs for an epitope that is different from the immunodominant one.

The Novel Anti Trop-2 mAbs Recognize a Non-Linear Glycosylated Epitope in the Processed Trop-2 Extracellular Domain.

The extracellular domain of Trop-2 contains asparagine (N) residues which are sites for N-linked glycosylation. N-linked glycosylation is one of the most abundant post-translational modifications of membrane proteins, with a direct effect on biological processes such as protein biosynthesis, localization, stability, intra- and inter-molecular interaction, immunity regulation. Cell surface glycosylation in tumors is known in the art to be different from that of non-transformed progenitor cells. Hence it was investigated whether the novel anti Trop-2 mAbs could specifically recognize the glycosylated target. To do this, site-specific mutagenesis was used to substitute either N120, N168 or N208 residue in the Trop-2 extracellular domain with alanine (A). KM12SM colon cancer cells transfected with these glycosylation-impaired Trop-2 mutants were subjected to flow cytometry analysis with the 1A9 mAb or with the benchmark T16 mAb. The T16 mAb was able to recognize Trop-2 irrespective of its glycosylation state (FIG. 15, top panels). On the contrary, the 1A9 antibody did not bind the N120A and the N208A mutants (FIG. 15A, C, bottom panels), while it surprisingly retained the ability to bind the N168A mutant (FIG. 15B, bottom panel). This showed that the novel anti Trop-2 mAbs generated according to the present invention specifically recognize a glycosylated epitope, such epitope being non-linear. Non-linear epitopes are formed by conformational alignment in the 3D structure of discontinuous amino acid sequences. The 3D structure of the Trop-2 molecule is known in the art (PDB ID: 7PEE). Mapping of the N120, N168 and N208 glycosylation residues onto such Trop-2 3D structure showed that indeed N120 and N208 are aligned along one side of the molecule, which defined the 1A9 binding surface, while N168 is excluded (FIG. 16A, B).

Therefore, the immunization and screening procedures described in the present invention made it possible to obtain new antibodies that recognize with high affinity the processed antigen expressed in cancer cells, and not the unprocessed antigen expressed in normal tissues. Mutagenesis combined with 3D structure analysis surprisingly showed that such antibodies recognize a non-linear epitope. Similar procedures can be applied to obtain antibodies for a variety of antigens that undergo specific and differential processing in tumor cells compared to normal tissues.

BIBLIOGRAPHY

Ambrogi, F., M. Fornili, P. Boracchi, M. Trerotola, V. Relli, P. Simeone, R. La Sorda, R. Lattanzio, P. Querzoli, M. Pedriali, M. Piantelli, E. Biganzoli and S. Alberti (2014). "Trop-2 is a determinant of breast cancer survival." *PLoS One* 9(5): e96993.

Bai, S., M. W. Nasser, B. Wang, S. H. Hsu, J. Datta, H. Kutay, A. Yadav, G. Nuovo, P. Kumar and K. Ghoshal (2009). "MicroRNA-122 inhibits tumorigenic properties of hepatocellular carcinoma cells and sensitizes these cells to sorafenib." *J Biol Chem* 284(46): 32015-32027.

Bardia, A., I. A. Mayer, L T. Vahdat, S. M. Tolaney, S. J. Isakoff, J. R. Diamond, J. O'Shaughnessy, R. L. Moroose, A. D. Santin, V. G. Abramson, N. C. Shah, H. S. Rugo, D. M. Goldenberg, A. M. Sweidan, R. Iannone, S. Washkowitz, R. M. Sharkey, W. A. Wegener and K. Kalinsky (2019). "Sacituzumab Govitecan-hziy in Refractory Metastatic Triple-Negative Breast Cancer." *N Engl J Med* 380(8): 741-751.

Biganzoli, E., M. Pedriali, P. Querzoli, I. Nenci, S. Iacobelli, M. Piantelli and S. Alberti (2010). "Sentinel Node and Bone Marrow Micrometastases and Nanometastases." *Curr Breast Cancer Rep* 2: 96-106.

Brummelkamp, T. R., R. Bernards and R. Agami (2002). "A System for Stable Expression of Short Interfering RNAs in Mammalian Cells." *Science* 296(5567): 550-553.

de Bono, J. S., A. W. Tolcher, A. Forero, G. F. Vanhove, C. Takimoto, R. J. Bauer, L. A. Hammond, A. Patnaik, M. L White, S. Shen, M. B. Khazaeli, E. K. Rowinsky and A. F. LoBuglio (2004). "ING-1, a monoclonal antibody targeting Ep-CAM in patients with advanced adenocarcinomas." *Clin Cancer Res* 10(22): 7555-7565.

El Sewedy, T., M. Fornaro and S. Alberti (1998). "Cloning of the murine Trop2 gene: conservation of a PIP2-binding sequence in the cytoplasmic domain of Trop-2." *Int J Cancer* 75(2): 324-330.

Elbashir, S. M., J. Harborth, W. Lendeckel, A. Yalcin, K. Weber and T. Tuschl (2001). "Duplexes of 21-nucleotide RNAs mediate RNA interference in cultured mammalian cells." *Nature* 411(6836): 494-498.

Fogel, M., P. Gutwein, S. Mechtersheimer, S. Riedle, A. Stoeck, A. Smirnov, L Edler, A. Ben-Arie, M. Huszar and P. Altevogt (2003). "L1 expression as a predictor of progression and survival in patients with uterine and ovarian carcinomas." *Lancet* 362(9387): 869-875.

Fradet, Y., C. Cordon-Cardo, T. Thomson, M. E. Daly, W. F. Whitmore Jr, K. O. Lloyd, M. R. Melamed and L G. Old (1984). "Cell-surface antigens of human bladder cancer defined by mouse monoclonal antibodies." *Proc. Natl. Acad. Sci. USA* 81: 224-228.

Fradet, Y., C. Cordon-Cardo, W. F. Whitmore, Jr., M. R. Melamed and L J. Old (1986). "Cell surface antigens of human bladder tumors: definition of tumor subsets by monoclonal antibodies and correlation with growth characteristics." *Cancer Res* 46(10): 5183-5188.

Gavert, N., M. Conacci-Sorrell, D. Gast, A. Schneider, P. Altevogt, T. Brabletz and A. Ben-Ze'ev (2005). "L1, a novel target of beta-catenin signaling, transforms cells and is expressed at the invasive front of colon cancers." *J Cell Biol* 168(4): 633-642.

Guerra, E., M. Trerotola, R. Dell' Arciprete, V. Bonasera, B. Palombo, T. El-Sewedy, T. Ciccimarra, C. Crescenzi, F. Lorenzini, C. Rossi, G. Vacca, R. Lattanzio, M. Piantelli and S. Alberti (2008). "A bi-cistronic CYCLIN D1-TROP2 mRNA chimera demonstrates a novel oncogenic mechanism in human cancer." *Cancer Res* 68(19): 8113-8121.

Guerra, E., M. Trerotola, R. Tripaldi, A. L. Aloisi, P. Simeone, A. Sacchetti, V. Relli, D. A. A, R. La Sorda, R. Lattanzio, M. Piantelli and S. Alberti (2016). "Trop-2 induces tumor growth through Akt and determines sensitivity to Akt inhibitors." *Clin Cancer Res* 22(16): 4197-4205.

Guncar, G., G. Pungercic, I. Klemencic, V. Turk and D. Turk (1999). "Crystal structure of MHC class II-associated p41 Ii fragment bound to cathepsin L reveals the structural basis for differentiation between cathepsins L and S." *EMBO J.* 18: 793-803.

Ikeda, M., M. Yamaguchi, K. Kato, K. Nakamura, S. Shiina, T. Ichikawa-Ando, H. Misaka, K. Myojo, Y. Sugimoto and H. Hamada (2015). "Pr1E11, a novel anti-TROP-2 antibody isolated by adenovirus-based antibody screening, recognizes a unique epitope." *Biochem Biophys Res Commun* 458(4): 877-882.

Kamble, P. R., S. Rane, A. A. Breed, S. Joseph, S. D. Mahale and B. R. Pathak (2020). "Proteolytic cleavage of Trop2 at Arg87 is mediated by matriptase and regulated by Val194." *FEBS Letters* 594(19): 3156-3169.

King, G. T., K. D. Eaton, B. R. Beagle, C. J. Zopf, G. Y. Wong, H. I. Krupka, S. Y. Hua, W. A. Messersmith and A. B. El-Khoueiry (2018). "A phase 1, dose-escalation study of PF-06664178, an anti-Trop-2/Aur0101 antibody-drug conjugate in patients with advanced or metastatic solid tumors." *Investigational New Drugs.*

Ko, S. Y., S. C. Lin, Y. K. Wong, C. J. Liu, K. W. Chang and T. Y. Liu (2007). "Increase of disintergin metalloprotease 10 (ADAM10) expression in oral squamous cell carcinoma." *Cancer Lett* 245(1-2): 33-43.

Lipinski, M., D. R. Parks, R. V. Rouse and L A. Herzenberg (1981). "Human trophoblast cell-surface antigens defined by monoclonal antibodies." *Proc. Natl. Acad. Sci. USA* 78: 5147-5150.

Morikawa, K., S. M. Walker, J. M. Jessup and I. J. Fidler (1988). "In vivo selection of highly metastatic cells from surgical specimens of different primary human colon carcinomas implanted into nude mice." *Cancer Res* 48(7): 1943-1948.

Pappin, D. J., P. Hojrup and A. J. Bleasby (1993). "Rapid identification of proteins by peptide-mass fingerprinting." *Curr Biol* 3(6): 327-332.

Querzoli, P., M. Pedriali, R. Rinaldi, A. R. Lombardi, E. Biganzoli, P. Boracchi, S. Ferretti, C. Frasson, C. Zanella, S. Ghisellini, F. Ambrogi, L Antolini, M. Piantelli, S. lacobelli, E. Marubini, S. Alberti and I. Nenci (2006). "Axillary lymph node nanometastases are prognostic factors for disease-free survival and metastatic relapse in breast cancer patients." *Clin. Cancer Res.* 12(22): 6696-6701.

Rossi, C., A. Di Lena, R. La Sorda, R. Lattanzio, L Antolini, C. Patassini, M. Piantelli and S. Alberti (2008). "Intestinal tumour chemoprevention with the antioxidant lipoic acid stimulates the growth of breast cancer." *Eur J Cancer* 44: 2696-2704.

Schon, M. P. and C. E. Orfanos (1995). "Transformation of human keratinocytes is characterized by quantitative and qualitative alterations of the T-16 antigen (Trop-2, MOv-16)." *Int J Cancer* 60(1): 88-92.

Schön, M. P., M. Schön, M. J. Mattes, R. Stein, L. Weber, S. Alberti and C. E. Klein (1993). "Biochemical and immunological characterization of the human carcinoma-associated antigen MH 99/KS 1/4." *Int. J. Cancer* 55: 988-995.

Schramme, A., M. S. Abdel-Bakky, N. Kampfer-Kolb, J. Pfeilschifter and P. Gutwein (2008). "The role of CXCL16 and its processing metalloproteinases ADAM10 and ADAM17 in the proliferation and migration of human mesangial cells." *Biochem Biophys Res Commun* 370(2): 311-316.

Stoyanova, T., A. S. Goldstein, H. Cai, J. M. Drake, J. Huang and O. N. Witte (2012). "Regulated proteolysis of Trop2 drives epithelial hyperplasia and stem cell self-renewal via beta-catenin signaling." *Genes Dev* 26(20): 2271-2285.

Tijink, B. M., J. Buter, R. de Bree, G. Giaccone, M. S. Lang, A. Staab, C. R. Leemans and G. A. M. S. van Dongen (2006). "A Phase I Dose Escalation Study with Anti-CD44v6 Bivatuzumab Mertansine in Patients with Incurable Squamous Cell Carcinoma of the Head and Neck or Esophagus." *Clinical Cancer Research* 12(20): 6064.

Trerotola, M., P. Cantanelli, E. Guerra, R. Tripaldi, A. L. Aloisi, V. Bonasera, R. Lattanzio, R. de Lange, U. H. Weidle, M. Piantelli and S. Alberti (2013). "Up-regulation of Trop-2 quantitatively stimulates human cancer growth." *Oncogene* 32 222-233.

Trerotola, M., S. Rathore, H. L. Goel, J. Li, S. Alberti, M. Piantelli, D. Adams, Z. Jiang and L. R. Languino (2010). "CD133, Trop-2 and alpha2beta1 integrin surface receptors as markers of putative human prostate cancer stem cells." *Am J Transl Res* 2(2): 135-144.

Tsujikawa, M., H. Kurahashi, T. Tanaka, K. Nishida, Y. Shimomura, Y. Tano and Y. Nakamura (1999). "Identification of the gene responsible for gelatinous drop-like corneal dystrophy." *Nat. Genet.* 21: 420-423.

Wang, Y. Y., Z. Y. Ye, L Li, Z. S. Zhao, Q. S. Shao and H. Q. Tao (2011). "ADAM 10 is associated with gastric cancer progression and prognosis of patients." *J Surg Oncol* 103(2): 116-123.

Wu, C. J., M. Lu, X. Feng, G. Nakato and M. C. Udey (2020). "Matriptase Cleaves EpCAM and TROP2 in Keratinocytes, Destabilizing Both Proteins and Associated Claudins." *Cells* 9(4).

Zanna, P., M. Trerotola, G. Vacca, V. Bonasera, B. Palombo, E. Guerra, C. Rossi, R. Lattanzio, M. Piantelli and S. Alberti (2007). "Trop-1 Are Conserved Growth Stimulatory Molecules That Mark Early Stages of Tumor Progression." *Cancer* 110(2): 452-464.

The invention claimed is:

1. A method to obtain monoclonal antibodies, or fragments or conjugates thereof, which bind with high affinity to a target protein which is a protein specifically expressed in local and metastatic tumors selected from the group consisting of cancers of the breast, head and neck, skin, colon-rectum, stomach, lung, ovary, thyroid, prostate, pancreas, endometrium, cervix, gallbladder, bile ducts, kidney, urinary bladder and choriocarcinomas and their metastases, wherein said method comprises:

making available an immunogenic material, wherein the immunogenic material is a non-linear epitope on the Trop-2 protein cleaved between R87 and T88, wherein the 3D structure of the Trop-2 molecule is according to PDB ID: 7PEE, said non-linear epitope being on the side of the molecule wherein the glycosylation residues N120 and N208 are aligned, excluding glycosylation site N168, wherein the residue numbering is according to SEQ ID NO. 1;

administering to a non-human animal said immunogenic material.

2. The method according to claim 1, to obtain monoclonal antibodies or fragments or conjugates thereof for use as a medicament, for use in the prevention and/or treatment of tumors and metastases that express Trop-2.

3. The method according to claim 1, to obtain monoclonal antibodies or fragments or conjugates thereof for use in diagnosing and/or assessing the risk of developing and/or prognosing and/or for monitoring the progression and/or for monitoring the efficacy of a therapeutic treatment and/or for the screening of a therapeutic treatment of a tumor or metastasis in a subject.

4. An antibody specific for Trop-2 protein expressed in local or metastatic tumor, wherein said antibody binds to a non-linear epitope on Trop-2 wherein the 3D structure of the Trop-2 molecule is according to PDB ID: 7PEE, said non-linear epitope includes the glycosylation residues N120 and N208 and being on the side of the molecule wherein the glycosylation residues N120 and N208 are aligned, excluding glycosylation site N168, wherein the residue numbering is according to SEQ ID NO. 1.

5. The antibody according to claim 4, wherein said antibody is 1B4 anti-Trop-2 monoclonal antibody, secreted by the hybridoma deposited with the International Depositary Authority (IDA): Interlab Cell Line Collection, IRCCS Ospedale Policlinico San Martino, Genova, Italy, and assigned accession number PD21005.

6. The antibody according to claim 4, wherein said antibody is 1A9 anti-Trop-2 monoclonal antibody, secreted by the hybridoma deposited with the International Depositary Authority (IDA): Interlab Cell Line Collection, IRCCS Ospedale Policlinico San Martino, Genova, Italy, and assigned accession number PD21006.

7. A pharmaceutical composition comprising at least one antibody according to claim 4.

8. The pharmaceutical composition according to claim 7, for use in a method for treating a human subject for a cancer.

* * * * *

SEQUENCE LISTING

```
<160> NUMBER OF SEQ ID NOS: 73

<210> SEQ ID NO 1
<211> LENGTH: 323
<212> TYPE: PRT
<213> ORGANISM: Homo sapiens

<400> SEQUENCE: 1

Met Ala Arg Gly Pro Gly Leu Ala Pro Pro Pro Leu Arg Leu Pro Leu
1               5                   10                  15
```

```
Leu Leu Leu Val Leu Ala Ala Val Thr Gly His Thr Ala Ala Gln Asp
            20                  25                  30

Asn Cys Thr Cys Pro Thr Asn Lys Met Thr Val Cys Ser Pro Asp Gly
        35                  40                  45

Pro Gly Gly Arg Cys Gln Cys Arg Ala Leu Gly Ser Gly Met Ala Val
    50                  55                  60

Asp Cys Ser Thr Leu Thr Ser Lys Cys Leu Leu Leu Lys Ala Arg Met
65                  70                  75                  80

Ser Ala Pro Lys Asn Ala Arg Thr Leu Val Arg Pro Ser Glu His Ala
                85                  90                  95

Leu Val Asp Asn Asp Gly Leu Tyr Asp Pro Asp Cys Asp Pro Glu Gly
            100                 105                 110

Arg Phe Lys Ala Arg Gln Cys Asn Gln Thr Ser Val Cys Trp Cys Val
        115                 120                 125

Asn Ser Val Gly Val Arg Arg Thr Asp Lys Gly Asp Leu Ser Leu Arg
    130                 135                 140

Cys Asp Glu Leu Val Arg Thr His His Ile Leu Ile Asp Leu Arg His
145                 150                 155                 160

Arg Pro Thr Ala Gly Ala Phe Asn His Ser Asp Leu Asp Ala Glu Leu
                165                 170                 175

Arg Arg Leu Phe Arg Glu Arg Tyr Arg Leu His Pro Lys Phe Val Ala
            180                 185                 190

Ala Val His Tyr Glu Gln Pro Thr Ile Gln Ile Glu Leu Arg Gln Asn
        195                 200                 205

Thr Ser Gln Lys Ala Ala Gly Asp Val Asp Ile Gly Asp Ala Ala Tyr
    210                 215                 220

Tyr Phe Glu Arg Asp Ile Lys Gly Glu Ser Leu Phe Gln Gly Arg Gly
225                 230                 235                 240

Gly Leu Asp Leu Arg Val Arg Gly Glu Pro Leu Gln Val Glu Arg Thr
                245                 250                 255

Leu Ile Tyr Tyr Leu Asp Glu Ile Pro Pro Lys Phe Ser Met Lys Arg
            260                 265                 270

Leu Thr Ala Gly Leu Ile Ala Val Ile Val Val Val Val Val Ala Leu
        275                 280                 285

Val Ala Gly Met Ala Val Leu Val Ile Thr Asn Arg Arg Lys Ser Gly
    290                 295                 300

Lys Tyr Lys Lys Val Glu Ile Lys Glu Leu Gly Glu Leu Arg Lys Glu
305                 310                 315                 320

Pro Ser Leu


<210> SEQ ID NO 2
<211> LENGTH: 10
<212> TYPE: PRT
<213> ORGANISM: Homo sapiens

<400> SEQUENCE: 2

Thr Leu Val Arg Pro Ser Glu His Ala Leu
1               5                   10


<210> SEQ ID NO 3
<211> LENGTH: 9
<212> TYPE: PRT
<213> ORGANISM: Homo sapiens

<400> SEQUENCE: 3

Glu Val His His Gln Lys Leu Val Phe
```

1 5

<210> SEQ ID NO 4
<211> LENGTH: 9
<212> TYPE: PRT
<213> ORGANISM: Homo sapiens

<400> SEQUENCE: 4

Gly Val Val Ile Ala Thr Val Ile Val
1 5

<210> SEQ ID NO 5
<211> LENGTH: 9
<212> TYPE: PRT
<213> ORGANISM: Homo sapiens

<400> SEQUENCE: 5

Val Gly Gly Val Val Ile Ala Thr Val
1 5

<210> SEQ ID NO 6
<211> LENGTH: 9
<212> TYPE: PRT
<213> ORGANISM: Homo sapiens

<400> SEQUENCE: 6

Val His His Gln Lys Leu Val Phe Phe
1 5

<210> SEQ ID NO 7
<211> LENGTH: 9
<212> TYPE: PRT
<213> ORGANISM: Homo sapiens

<400> SEQUENCE: 7

Ala Asn His Met Ala Ala Gln Pro Gln
1 5

<210> SEQ ID NO 8
<211> LENGTH: 9
<212> TYPE: PRT
<213> ORGANISM: Homo sapiens

<400> SEQUENCE: 8

Glu His Ala Asn His Met Ala Ala Gln
1 5

<210> SEQ ID NO 9
<211> LENGTH: 9
<212> TYPE: PRT
<213> ORGANISM: Homo sapiens

<400> SEQUENCE: 9

Ala Thr Val Val Ile Val Val Cys Val
1 5

<210> SEQ ID NO 10
<211> LENGTH: 9
<212> TYPE: PRT
<213> ORGANISM: Homo sapiens

<400> SEQUENCE: 10

Pro Ser Thr Ala Thr Val Val Ile Val
1 5

<210> SEQ ID NO 11
<211> LENGTH: 9
<212> TYPE: PRT
<213> ORGANISM: Homo sapiens

<400> SEQUENCE: 11

Glu His Val Asn His Leu Ile Val Gln
1 5

<210> SEQ ID NO 12
<211> LENGTH: 9
<212> TYPE: PRT
<213> ORGANISM: Homo sapiens

<400> SEQUENCE: 12

Ala Thr Val Val Ile Ile Ile Ser Val
1 5

<210> SEQ ID NO 13
<211> LENGTH: 9
<212> TYPE: PRT
<213> ORGANISM: Homo sapiens

<400> SEQUENCE: 13

Pro Ser Ile Ala Thr Val Val Ile Ile
1 5

<210> SEQ ID NO 14
<211> LENGTH: 9
<212> TYPE: PRT
<213> ORGANISM: Homo sapiens

<400> SEQUENCE: 14

Ala His Pro Ser His Val Leu Ser Ser
1 5

<210> SEQ ID NO 15
<211> LENGTH: 9
<212> TYPE: PRT
<213> ORGANISM: Homo sapiens

<400> SEQUENCE: 15

Ala Thr Leu Ile Ile Val Val Cys Val
1 5

<210> SEQ ID NO 16
<211> LENGTH: 9
<212> TYPE: PRT
<213> ORGANISM: Homo sapiens

<400> SEQUENCE: 16

Pro Ser Ala Ala Thr Leu Ile Ile Val
1 5

<210> SEQ ID NO 17
<211> LENGTH: 9
<212> TYPE: PRT
<213> ORGANISM: Homo sapiens

<400> SEQUENCE: 17

Asn Ser Phe Glu Met Gln Lys Gly Asp
1 5

<210> SEQ ID NO 18

<211> LENGTH: 9
<212> TYPE: PRT
<213> ORGANISM: Homo sapiens

<400> SEQUENCE: 18

Leu Ser Glu Arg His Met Glu Ser Gln
1 5

<210> SEQ ID NO 19
<211> LENGTH: 7
<212> TYPE: PRT
<213> ORGANISM: Homo sapiens

<400> SEQUENCE: 19

Ala Glu Tyr Ser Ile Lys Glu
1 5

<210> SEQ ID NO 20
<211> LENGTH: 9
<212> TYPE: PRT
<213> ORGANISM: Homo sapiens

<400> SEQUENCE: 20

Thr Pro Ser Lys Glu Arg Asn Gly Leu
1 5

<210> SEQ ID NO 21
<211> LENGTH: 9
<212> TYPE: PRT
<213> ORGANISM: Homo sapiens

<400> SEQUENCE: 21

Lys Lys Lys Gly Lys Gly Leu Gly Lys
1 5

<210> SEQ ID NO 22
<211> LENGTH: 9
<212> TYPE: PRT
<213> ORGANISM: Homo sapiens

<400> SEQUENCE: 22

Glu Asn Pro Leu Tyr Thr Tyr Asp His
1 5

<210> SEQ ID NO 23
<211> LENGTH: 9
<212> TYPE: PRT
<213> ORGANISM: Homo sapiens

<400> SEQUENCE: 23

Thr Asn Met Lys His Met Ala Gly Ala
1 5

<210> SEQ ID NO 24
<211> LENGTH: 7
<212> TYPE: PRT
<213> ORGANISM: Homo sapiens

<400> SEQUENCE: 24

Ala Tyr Tyr Asp Gly Arg Ser
1 5

<210> SEQ ID NO 25
<211> LENGTH: 9
<212> TYPE: PRT

<213> ORGANISM: Homo sapiens

<400> SEQUENCE: 25

Tyr Leu Ala Ser Ala Ser Thr Met Asp
1 5

<210> SEQ ID NO 26
<211> LENGTH: 9
<212> TYPE: PRT
<213> ORGANISM: Homo sapiens

<400> SEQUENCE: 26

Gly His His Ala Ala Arg Thr Thr His
1 5

<210> SEQ ID NO 27
<211> LENGTH: 9
<212> TYPE: PRT
<213> ORGANISM: Homo sapiens

<400> SEQUENCE: 27

Tyr Gly Ser Leu Pro Gln Lys Ala Gln
1 5

<210> SEQ ID NO 28
<211> LENGTH: 9
<212> TYPE: PRT
<213> ORGANISM: Homo sapiens

<400> SEQUENCE: 28

Tyr Lys Ser Leu Pro Gln Lys Ser Gln
1 5

<210> SEQ ID NO 29
<211> LENGTH: 9
<212> TYPE: PRT
<213> ORGANISM: Homo sapiens

<400> SEQUENCE: 29

Tyr Lys Ile Glu Ala Val Lys Ser Glu
1 5

<210> SEQ ID NO 30
<211> LENGTH: 9
<212> TYPE: PRT
<213> ORGANISM: Homo sapiens

<400> SEQUENCE: 30

Gly Ser Ser Gln Pro Val Val Thr Arg
1 5

<210> SEQ ID NO 31
<211> LENGTH: 9
<212> TYPE: PRT
<213> ORGANISM: Homo sapiens

<400> SEQUENCE: 31

Gln Pro Val Val Thr Arg Gly Thr Thr
1 5

<210> SEQ ID NO 32
<211> LENGTH: 9
<212> TYPE: PRT
<213> ORGANISM: Homo sapiens

<400> SEQUENCE: 32

Pro Val Ala Ala Ala Val Val Ser His
1 5

<210> SEQ ID NO 33
<211> LENGTH: 9
<212> TYPE: PRT
<213> ORGANISM: Homo sapiens

<400> SEQUENCE: 33

Pro Leu Ala Gln Ala Val Arg Ser Ser
1 5

<210> SEQ ID NO 34
<211> LENGTH: 9
<212> TYPE: PRT
<213> ORGANISM: Homo sapiens

<400> SEQUENCE: 34

Ser Pro Glu Thr Asn Leu Leu Cys Gly
1 5

<210> SEQ ID NO 35
<211> LENGTH: 9
<212> TYPE: PRT
<213> ORGANISM: Homo sapiens

<400> SEQUENCE: 35

Val Asp Leu Phe Tyr Leu Arg Gly Asp
1 5

<210> SEQ ID NO 36
<211> LENGTH: 8
<212> TYPE: PRT
<213> ORGANISM: Homo sapiens

<400> SEQUENCE: 36

Tyr Ser Val Arg Asn Ser Asp Ser
1 5

<210> SEQ ID NO 37
<211> LENGTH: 9
<212> TYPE: PRT
<213> ORGANISM: Homo sapiens

<400> SEQUENCE: 37

Trp Trp Glu Leu Arg His Ala Gly His
1 5

<210> SEQ ID NO 38
<211> LENGTH: 9
<212> TYPE: PRT
<213> ORGANISM: Homo sapiens

<400> SEQUENCE: 38

Arg Lys Ala Gln Pro Val Glu Ala Gly
1 5

<210> SEQ ID NO 39
<211> LENGTH: 9
<212> TYPE: PRT
<213> ORGANISM: Homo sapiens

<400> SEQUENCE: 39

Thr Asp Val Asp Arg Ile Val Gly Ala
1 5

<210> SEQ ID NO 40
<211> LENGTH: 9
<212> TYPE: PRT
<213> ORGANISM: Homo sapiens

<400> SEQUENCE: 40

Ala Glu Gln Gln Arg Leu Lys Ser Gln
1 5

<210> SEQ ID NO 41
<211> LENGTH: 9
<212> TYPE: PRT
<213> ORGANISM: Homo sapiens

<400> SEQUENCE: 41

Gly Asp Gln Met Ala Gln Lys Ser Gln
1 5

<210> SEQ ID NO 42
<211> LENGTH: 9
<212> TYPE: PRT
<213> ORGANISM: Homo sapiens

<400> SEQUENCE: 42

Leu Arg Ala Glu Gln Gln Arg Leu Lys
1 5

<210> SEQ ID NO 43
<211> LENGTH: 9
<212> TYPE: PRT
<213> ORGANISM: Homo sapiens

<400> SEQUENCE: 43

Leu Arg Ala Glu Gln Gln Arg Leu Lys
1 5

<210> SEQ ID NO 44
<211> LENGTH: 9
<212> TYPE: PRT
<213> ORGANISM: Homo sapiens

<400> SEQUENCE: 44

Ser Ser Leu Glu Lys Gln Ile Gly His
1 5

<210> SEQ ID NO 45
<211> LENGTH: 323
<212> TYPE: PRT
<213> ORGANISM: Homo sapiens

<400> SEQUENCE: 45

Met Ala Arg Gly Pro Gly Leu Ala Pro Pro Pro Leu Arg Leu Pro Leu
1 5 10 15

Leu Leu Leu Val Leu Ala Ala Val Thr Gly His Thr Ala Ala Gln Asp
20 25 30

Asn Cys Thr Cys Pro Thr Asn Lys Met Thr Val Cys Ser Pro Asp Gly
35 40 45

Pro Gly Gly Arg Cys Gln Cys Arg Ala Leu Gly Ser Gly Met Ala Val
50 55 60

Asp Cys Ser Thr Leu Thr Ser Lys Cys Leu Leu Leu Lys Ala Arg Met

```
65                  70                  75                  80

Ser Ala Pro Lys Asn Ala Ala Ala Leu Val Arg Pro Ser Glu His Ala
                85                  90                  95

Leu Val Asp Asn Asp Gly Leu Tyr Asp Pro Asp Cys Asp Pro Glu Gly
            100                 105                 110

Arg Phe Lys Ala Arg Gln Cys Asn Gln Thr Ser Val Cys Trp Cys Val
        115                 120                 125

Asn Ser Val Gly Val Arg Arg Thr Asp Lys Gly Asp Leu Ser Leu Arg
    130                 135                 140

Cys Asp Glu Leu Val Arg Thr His His Ile Leu Ile Asp Leu Arg His
145                 150                 155                 160

Arg Pro Thr Ala Gly Ala Phe Asn His Ser Asp Leu Asp Ala Glu Leu
                165                 170                 175

Arg Arg Leu Phe Arg Glu Arg Tyr Arg Leu His Pro Lys Phe Val Ala
            180                 185                 190

Ala Val His Tyr Glu Gln Pro Thr Ile Gln Ile Glu Leu Arg Gln Asn
        195                 200                 205

Thr Ser Gln Lys Ala Ala Gly Asp Val Asp Ile Gly Asp Ala Ala Tyr
    210                 215                 220

Tyr Phe Glu Arg Asp Ile Lys Gly Glu Ser Leu Phe Gln Gly Arg Gly
225                 230                 235                 240

Gly Leu Asp Leu Arg Val Arg Gly Glu Pro Leu Gln Val Glu Arg Thr
                245                 250                 255

Leu Ile Tyr Tyr Leu Asp Glu Ile Pro Pro Lys Phe Ser Met Lys Arg
            260                 265                 270

Leu Thr Ala Gly Leu Ile Ala Val Ile Val Val Val Val Val Ala Leu
        275                 280                 285

Val Ala Gly Met Ala Val Leu Val Ile Thr Asn Arg Arg Lys Ser Gly
    290                 295                 300

Lys Tyr Lys Lys Val Glu Ile Lys Glu Leu Gly Glu Leu Arg Lys Glu
305                 310                 315                 320

Pro Ser Leu


<210> SEQ ID NO 46
<211> LENGTH: 20
<212> TYPE: PRT
<213> ORGANISM: Homo sapiens

<400> SEQUENCE: 46

Arg His Tyr Glu Gly Leu Ser Tyr Asn Val Asp Ser Leu His Gln Lys
1               5                   10                  15

His Gln Arg Ala
            20


<210> SEQ ID NO 47
<211> LENGTH: 15
<212> TYPE: PRT
<213> ORGANISM: Homo sapiens

<400> SEQUENCE: 47

Arg Gln Arg Pro Arg Glu Ser Tyr Gln Met Gly His Met Arg Arg
1               5                   10                  15


<210> SEQ ID NO 48
<211> LENGTH: 18
<212> TYPE: PRT
<213> ORGANISM: Homo sapiens
```

<400> SEQUENCE: 48

Arg Ala His Pro Glu Lys His Ala Ala Ser Ser Gly Pro Glu Leu Leu
1 5 10 15

Arg Lys

<210> SEQ ID NO 49
<211> LENGTH: 14
<212> TYPE: PRT
<213> ORGANISM: Homo sapiens

<400> SEQUENCE: 49

Arg Glu Ala Val Ile Ala Gln Ile Ser Ser His Val Lys Ala
1 5 10

<210> SEQ ID NO 50
<211> LENGTH: 749
<212> TYPE: PRT
<213> ORGANISM: Homo sapiens

<400> SEQUENCE: 50

Met Val Leu Leu Arg Val Leu Ile Leu Leu Leu Ser Trp Ala Ala Gly
1 5 10 15

Leu Gly Gly Gln Tyr Gly Asn Pro Leu Asn Lys Tyr Ile Arg His Tyr
20 25 30

Glu Gly Leu Ser Tyr Asn Val Asp Ser Leu His Gln Lys His Gln Arg
35 40 45

Ala Lys Arg Ala Val Ser His Glu Asp Gln Phe Leu Leu Leu Asp Phe
50 55 60

His Ala His Gly Arg Gln Phe Asn Leu Arg Met Lys Arg Asp Thr Ser
65 70 75 80

Leu Phe Ser Asp Glu Phe Lys Val Glu Thr Ser Asn Lys Val Leu Asp
85 90 95

Tyr Asp Thr Ser His Ile Tyr Thr Gly His Ile Tyr Gly Glu Glu Gly
100 105 110

Ser Phe Ser His Gly Ser Val Ile Asp Gly Arg Phe Glu Gly Phe Ile
115 120 125

Lys Thr Arg Gly Gly Thr Phe Tyr Ile Glu Pro Ala Glu Arg Tyr Ile
130 135 140

Lys Asp Arg Ile Leu Pro Phe His Ser Val Ile Tyr His Glu Asp Asp
145 150 155 160

Ile Asn Tyr Pro His Lys Tyr Gly Pro Gln Gly Gly Cys Ala Asp His
165 170 175

Ser Val Phe Glu Arg Met Arg Lys Tyr Gln Met Thr Gly Val Glu Glu
180 185 190

Gly Ala Arg Ala His Pro Glu Lys His Ala Ala Ser Ser Gly Pro Glu
195 200 205

Leu Leu Arg Lys Lys Arg Thr Thr Leu Ala Glu Arg Asn Thr Cys Gln
210 215 220

Leu Tyr Ile Gln Thr Asp His Leu Phe Phe Lys Tyr Tyr Gly Thr Arg
225 230 235 240

Glu Ala Val Ile Ala Gln Ile Ser Ser His Val Lys Ala Ile Asp Thr
245 250 255

Ile Tyr Gln Thr Thr Asp Phe Ser Gly Ile Arg Asn Ile Ser Phe Met
260 265 270

Val Lys Arg Ile Arg Ile Asn Thr Thr Ser Asp Glu Lys Asp Pro Thr

```
        275                 280                 285

Asn Pro Phe Arg Phe Pro Asn Ile Gly Val Glu Lys Phe Leu Glu Leu
    290                 295                 300

Asn Ser Glu Gln Asn His Asp Asp Tyr Cys Leu Ala Tyr Val Phe Thr
305                 310                 315                 320

Asp Arg Asp Phe Asp Asp Gly Val Leu Gly Leu Ala Trp Val Gly Ala
                325                 330                 335

Pro Ser Gly Ser Ser Gly Gly Ile Cys Glu Lys Ser Lys Leu Tyr Ser
            340                 345                 350

Asp Gly Lys Lys Lys Ser Leu Asn Thr Gly Ile Ile Thr Val Gln Asn
        355                 360                 365

Tyr Gly Ser His Val Pro Pro Lys Val Ser His Ile Thr Phe Ala His
    370                 375                 380

Glu Val Gly His Asn Phe Gly Ser Pro His Asp Ser Gly Thr Glu Cys
385                 390                 395                 400

Thr Pro Gly Glu Ser Lys Asn Leu Gly Gln Lys Glu Asn Gly Asn Tyr
                405                 410                 415

Ile Met Tyr Ala Arg Ala Thr Ser Gly Asp Lys Leu Asn Asn Asn Lys
            420                 425                 430

Phe Ser Leu Cys Ser Ile Arg Asn Ile Ser Gln Val Leu Glu Lys Lys
        435                 440                 445

Arg Asn Asn Cys Phe Val Glu Ser Gly Gln Pro Ile Cys Gly Asn Gly
    450                 455                 460

Met Val Glu Gln Gly Glu Glu Cys Asp Cys Gly Tyr Ser Asp Gln Cys
465                 470                 475                 480

Lys Asp Asp Cys Cys Phe Asp Ala Asn Gln Pro Glu Gly Lys Lys Cys
                485                 490                 495

Lys Leu Lys Pro Gly Lys Gln Cys Ser Pro Ser Gln Gly Pro Cys Cys
            500                 505                 510

Thr Ala Gln Cys Ala Phe Lys Ser Lys Ser Glu Lys Cys Arg Asp Asp
        515                 520                 525

Ser Asp Cys Ala Lys Glu Gly Ile Cys Asn Gly Phe Thr Ala Leu Cys
    530                 535                 540

Pro Ala Ser Asp Pro Lys Pro Asn Phe Thr Asp Cys Asn Arg His Thr
545                 550                 555                 560

Gln Val Cys Ile Asn Gly Gln Cys Ala Gly Ser Ile Cys Glu Lys Tyr
                565                 570                 575

Asp Leu Glu Glu Cys Thr Cys Ala Ser Ser Asp Gly Lys Asp Asn Lys
            580                 585                 590

Glu Leu Cys His Val Cys Cys Met Lys Lys Met Ala Pro Ser Thr Cys
        595                 600                 605

Ala Ser Thr Gly Ser Leu Gln Trp Ser Lys Gln Phe Ser Gly Arg Thr
    610                 615                 620

Ile Thr Leu Gln Pro Gly Ser Pro Cys Asn Asp Phe Arg Gly Tyr Cys
625                 630                 635                 640

Asp Val Phe Met Arg Cys Arg Leu Val Asp Ala Asp Gly Pro Leu Ala
                645                 650                 655

Arg Leu Lys Lys Ala Ile Phe Ser Pro Gln Leu Tyr Glu Asn Ile Ala
            660                 665                 670

Glu Trp Ile Val Ala His Trp Trp Ala Val Leu Leu Met Gly Ile Ala
        675                 680                 685

Leu Ile Met Leu Met Ala Gly Phe Ile Lys Ile Cys Ser Val His Thr
    690                 695                 700
```

```
Pro Ser Ser Asn Pro Lys Leu Pro Pro Pro Lys Pro Leu Pro Gly Thr
705                 710                 715                 720

Leu Lys Arg Arg Arg Pro Pro Gln Pro Ile Gln Gln Pro Pro Arg Gln
                725                 730                 735

Arg Pro Arg Glu Ser Tyr Gln Met Gly His Met Arg Arg
            740                 745
```

<210> SEQ ID NO 51
<211> LENGTH: 30
<212> TYPE: DNA
<213> ORGANISM: Homo sapiens

<400> SEQUENCE: 51
ctcggatcca tggctcgggg ccccggcctc 30

<210> SEQ ID NO 52
<211> LENGTH: 30
<212> TYPE: DNA
<213> ORGANISM: Homo sapiens

<400> SEQUENCE: 52
ctcgaattcc aagctcggtt cctttctcaa 30

<210> SEQ ID NO 53
<211> LENGTH: 27
<212> TYPE: DNA
<213> ORGANISM: Homo sapiens

<400> SEQUENCE: 53
gcgattctcg agtccggtcc gcgttcc 27

<210> SEQ ID NO 54
<211> LENGTH: 27
<212> TYPE: DNA
<213> ORGANISM: Homo sapiens

<400> SEQUENCE: 54
gcgccggtac caagctcggt tcctttc 27

<210> SEQ ID NO 55
<211> LENGTH: 36
<212> TYPE: DNA
<213> ORGANISM: Homo sapiens

<400> SEQUENCE: 55
agcgccccca agaacgccgc cgcgctggtg cggccg 36

<210> SEQ ID NO 56
<211> LENGTH: 36
<212> TYPE: DNA
<213> ORGANISM: Homo sapiens

<400> SEQUENCE: 56
cggccgcacc agcgcggcgg cgttcttggg ggcgct 36

<210> SEQ ID NO 57
<211> LENGTH: 64
<212> TYPE: DNA
<213> ORGANISM: Mus musculus

<400> SEQUENCE: 57
gatccccaga cattatgaag gattatttca agagaataat ccttcataat gtctttttg 60 gaaa 64

<210> SEQ ID NO 58
<211> LENGTH: 64
<212> TYPE: DNA
<213> ORGANISM: Mus musculus

<400> SEQUENCE: 58
agcttttcca aaaaagacat tatgaaggat tattctcttg aaataatcct tcataatgtc 60
tggg 64

<210> SEQ ID NO 59
<211> LENGTH: 64
<212> TYPE: DNA
<213> ORGANISM: Mus musculus

<400> SEQUENCE: 59 gatcccccg cagaccaaga gggtttttca agagaaaacc ctcttggtct gcggtttttg 60
gaaa 64

<210> SEQ ID NO 60
<211> LENGTH: 64
<212> TYPE: DNA
<213> ORGANISM: Mus musculus

<400> SEQUENCE: 60
agcttttcca aaaaccgcag accaagaggg ttttctcttg aaaaaccctc ttggtctgcg 60
gggg 64

<210> SEQ ID NO 61
<211> LENGTH: 64
<212> TYPE: DNA
<213> ORGANISM: Homo sapiens

<400> SEQUENCE: 61
gatccccctt gacaacgtta ataacgttca agagacgtta ttaacgttgt caagtttttg 60
gaaa 64

<210> SEQ ID NO 62
<211> LENGTH: 64
<212> TYPE: DNA
<213> ORGANISM: Homo sapiens

<400> SEQUENCE: 62
agcttttcca aaaacttgac aacgttaata acgtctcttg aacgttatta acgttgtcaa 60
gggg 64

<210> SEQ ID NO 63
<211> LENGTH: 64
<212> TYPE: DNA
<213> ORGANISM: Homo sapiens

<400> SEQUENCE: 63
gatcccctgc aggaagtggt gggaatttca agagaattcc caccacttcc tgcatttttg 60
gaaa 64

<210> SEQ ID NO 64
<211> LENGTH: 64
<212> TYPE: DNA

<213> ORGANISM: Homo sapiens

<400> SEQUENCE: 64
agcttttcca aaaatgcagg aagtggtggg aattctcttg aaattcccac cacttcctgc 60
aggg 64

<210> SEQ ID NO 65
<211> LENGTH: 20
<212> TYPE: DNA
<213> ORGANISM: Mus musculus

<400> SEQUENCE: 65
agcaacatct ggggacaaac 20

<210> SEQ ID NO 66
<211> LENGTH: 20
<212> TYPE: DNA
<213> ORGANISM: Mus musculus

<400> SEQUENCE: 66
ttgcactggt cactgtagcc 20

<210> SEQ ID NO 67
<211> LENGTH: 19
<212> TYPE: DNA
<213> ORGANISM: Mus musculus

<400> SEQUENCE: 67
gtgcgaccac atcgaactt 19

<210> SEQ ID NO 68
<211> LENGTH: 20
<212> TYPE: DNA
<213> ORGANISM: Mus musculus

<400> SEQUENCE: 68
ggatgccgtc tatgtcgtct 20

<210> SEQ ID NO 69
<211> LENGTH: 20
<212> TYPE: DNA
<213> ORGANISM: Mus musculus

<400> SEQUENCE: 69
gagcccaaga ccgtctactg 20

<210> SEQ ID NO 70
<211> LENGTH: 24
<212> TYPE: DNA
<213> ORGANISM: Mus musculus

<400> SEQUENCE: 70
aaagaaggtg atgtgtacat tgct 24

<210> SEQ ID NO 71
<211> LENGTH: 236
<212> TYPE: PRT
<213> ORGANISM: Homo sapiens

<400> SEQUENCE: 71

Thr Leu Val Arg Pro Ser Glu His Ala Leu Val Asp Asn Asp Gly Leu
1 5 10 15

```
Tyr Asp Pro Asp Cys Asp Pro Glu Gly Arg Phe Lys Ala Arg Gln Cys
            20                  25                  30

Asn Gln Thr Ser Val Cys Trp Cys Val Asn Ser Val Gly Val Arg Arg
        35                  40                  45

Thr Asp Lys Gly Asp Leu Ser Leu Arg Cys Asp Glu Leu Val Arg Thr
    50                  55                  60

His His Ile Leu Ile Asp Leu Arg His Arg Pro Thr Ala Gly Ala Phe
65                  70                  75                  80

Asn His Ser Asp Leu Asp Ala Glu Leu Arg Arg Leu Phe Arg Glu Arg
                85                  90                  95

Tyr Arg Leu His Pro Lys Phe Val Ala Ala Val His Tyr Glu Gln Pro
            100                 105                 110

Thr Ile Gln Ile Glu Leu Arg Gln Asn Thr Ser Gln Lys Ala Ala Gly
        115                 120                 125

Asp Val Asp Ile Gly Asp Ala Ala Tyr Tyr Phe Glu Arg Asp Ile Lys
    130                 135                 140

Gly Glu Ser Leu Phe Gln Gly Arg Gly Gly Leu Asp Leu Arg Val Arg
145                 150                 155                 160

Gly Glu Pro Leu Gln Val Glu Arg Thr Leu Ile Tyr Tyr Leu Asp Glu
                165                 170                 175

Ile Pro Pro Lys Phe Ser Met Lys Arg Leu Thr Ala Gly Leu Ile Ala
            180                 185                 190

Val Ile Val Val Val Val Val Ala Leu Val Ala Gly Met Ala Val Leu
        195                 200                 205

Val Ile Thr Asn Arg Arg Lys Ser Gly Lys Tyr Lys Lys Val Glu Ile
    210                 215                 220

Lys Glu Leu Gly Glu Leu Arg Lys Glu Pro Ser Leu
225                 230                 235


<210> SEQ ID NO 72
<211> LENGTH: 57
<212> TYPE: PRT
<213> ORGANISM: Homo sapiens

<400> SEQUENCE: 72

Gln Asp Asn Cys Thr Cys Pro Thr Asn Lys Met Thr Val Cys Ser Pro
1               5                   10                  15

Asp Gly Pro Gly Gly Arg Cys Gln Cys Arg Ala Leu Gly Ser Gly Met
            20                  25                  30

Ala Val Asp Cys Ser Thr Leu Thr Ser Lys Cys Leu Leu Leu Lys Ala
        35                  40                  45

Arg Met Ser Ala Pro Lys Asn Ala Arg
    50                  55


<210> SEQ ID NO 73
<211> LENGTH: 323
<212> TYPE: PRT
<213> ORGANISM: Macaca mulatta

<400> SEQUENCE: 73

Met Ala Arg Gly Pro Gly Leu Ala Pro Pro Pro Leu Arg Leu Pro Leu
1               5                   10                  15

Leu Leu Leu Leu Leu Ala Ala Val Thr Gly His Thr Ala Ala Gln Asp
            20                  25                  30

Asn Cys Thr Cys Pro Thr Asn Lys Met Thr Val Cys Ser Pro Asp Gly
        35                  40                  45
```

-continued

```
Pro Gly Gly Arg Cys Gln Cys Arg Ala Leu Gly Ser Gly Val Ala Val
    50                  55                  60

Asp Cys Ser Thr Leu Thr Ser Lys Cys Leu Leu Leu Lys Ala Arg Met
65                  70                  75                      80

Ser Ala Pro Lys Asn Ala Arg Thr Leu Val Arg Pro Asn Glu His Ala
                85                  90                  95

Leu Val Asp Asn Asp Gly Leu Tyr Asp Pro Asp Cys Asp Pro Glu Gly
            100                 105                 110

Arg Phe Lys Ala Arg Gln Cys Asn Gln Thr Ser Val Cys Trp Cys Val
        115                 120                 125

Asn Ser Val Gly Val Arg Arg Thr Asp Lys Gly Asp Leu Ser Leu Arg
    130                 135                 140

Cys Asp Glu Leu Val Arg Thr His His Ile Leu Ile Asp Leu Arg His
145                 150                 155                     160

Arg Pro Thr Ala Gly Ala Phe Asn His Ser Asp Leu Asp Ala Glu Leu
                165                 170                 175

Arg Arg Leu Phe Arg Glu Arg Tyr Arg Leu His Pro Lys Phe Val Ala
            180                 185                 190

Ala Val His Tyr Glu Gln Pro Thr Ile Gln Ile Glu Leu Arg Gln Asn
        195                 200                 205

Thr Ser Gln Lys Ala Ala Gly Asp Val Asp Ile Gly Asp Ala Ala Tyr
    210                 215                 220

Tyr Phe Glu Arg Asp Val Lys Gly Glu Ser Leu Phe Gln Gly Arg Gly
225                 230                 235                     240

Gly Leu Asp Leu Arg Val Arg Gly Glu Pro Leu Gln Val Glu Arg Thr
                245                 250                 255

Leu Ile Tyr Tyr Leu Asp Glu Ile Pro Pro Lys Phe Ser Met Lys Arg
            260                 265                 270

Leu Thr Ala Gly Leu Ile Ala Val Ile Val Val Val Val Val Ala Leu
        275                 280                 285

Val Ala Gly Val Ala Val Leu Val Ile Ser Asn Arg Arg Lys Ser Gly
    290                 295                 300

Lys Tyr Lys Lys Val Glu Ile Lys Glu Leu Gly Glu Leu Arg Lys Glu
305                 310                 315                     320

Pro Ser Leu
```